United States Patent
Nishihara et al.

(10) Patent No.: US 10,074,804 B2
(45) Date of Patent: Sep. 11, 2018

(54) PICENE DERIVATIVE, PHOTOELECTRIC MATERIAL, AND PHOTOELECTRIC DEVICE

(71) Applicant: ADEKA CORPORATION, Tokyo (JP)

(72) Inventors: Yasushi Nishihara, Okayama (JP); Keita Hyodo, Okayama (JP); Hiroki Mori, Okayama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/504,425

(22) PCT Filed: Oct. 14, 2015

(86) PCT No.: PCT/JP2015/079033
§ 371 (c)(1),
(2) Date: Feb. 16, 2017

(87) PCT Pub. No.: WO2016/063771
PCT Pub. Date: Apr. 28, 2016

(65) Prior Publication Data
US 2017/0237011 A1   Aug. 17, 2017

(30) Foreign Application Priority Data
Oct. 21, 2014   (JP) ................. 2014-214551

(51) Int. Cl.
*H01L 29/08* (2006.01)
*H01L 51/00* (2006.01)
(Continued)

(52) U.S. Cl.
CPC ........ *H01L 51/0036* (2013.01); *C08G 61/126* (2013.01); *H01L 51/0043* (2013.01);
(Continued)

(58) Field of Classification Search
CPC ...................................................... C07C 15/20
(Continued)

(56) References Cited

U.S. PATENT DOCUMENTS 8,575,599 B2 * 11/2013 Nakano ............... C07C 15/20
257/40
2008/0083455 A1   4/2008 Li et al.
(Continued)

FOREIGN PATENT DOCUMENTS

GB   1027577   4/1966
JP   04-45162   2/1992
(Continued)

OTHER PUBLICATIONS

Padinger et al., "Effects of Postproduction Treatment on Plastic Solar Cells", Adv. Funct. Mater., 13, 85 (2003).
(Continued)

*Primary Examiner* — Khanh T Nguyen
(74) *Attorney, Agent, or Firm* — Young & Thompson

(57) ABSTRACT

The present invention provides: a p-type organic semiconductor material which is able to be produced easily, while having high planarity in a polymer skeleton; and a photoelectric conversion layer, a photoelectric conversion element and an organic thin film solar cell, each of which uses this p-type organic semiconductor material and has high photoelectric conversion efficiency. The present invention specifically provides: a picene derivative which has at least one constituent unit represented by general formula (1); and a photoelectric conversion element which contains (A) the picene derivative serving as a p-type organic semiconductor material and (B) an n-type organic semiconductor material. The details of general formula (1) are as set forth in the description.

9 Claims, 1 Drawing Sheet

(51) Int. Cl.
*C08G 61/12* (2006.01)
*H01L 51/42* (2006.01)

(52) U.S. Cl.
CPC .... *H01L 51/0047* (2013.01); *C08G 2261/124* (2013.01); *C08G 2261/1412* (2013.01); *C08G 2261/18* (2013.01); *C08G 2261/228* (2013.01); *C08G 2261/3223* (2013.01); *C08G 2261/3241* (2013.01); *C08G 2261/3243* (2013.01); *C08G 2261/3246* (2013.01); *C08G 2261/41* (2013.01); *C08G 2261/91* (2013.01); *H01L 51/4253* (2013.01)

(58) Field of Classification Search
USPC .......................................................... 257/40
See application file for complete search history.

(56) References Cited

U.S. PATENT DOCUMENTS

| | | |
|---|---|---|
| 2011/0049485 A1 | 3/2011 | Kim et al. |
| 2015/0108409 A1 | 4/2015 | Meyer et al. |
| 2015/0126751 A1 | 5/2015 | Doetz et al. |

FOREIGN PATENT DOCUMENTS

| | | | | |
|---|---|---|---|---|
| JP | 2009-158921 | | 7/2009 | |
| JP | 2009-218333 | * | 9/2009 | ............ H01L 51/30 |
| JP | 2011-116962 | | 6/2011 | |
| JP | 2011-236158 | | 11/2011 | |
| JP | 2013-170134 | | 9/2013 | |
| JP | 2014-058501 | * | 4/2014 | ............... C07C 1/30 |
| JP | 2014-240483 | | 12/2014 | |
| WO | WO 2013/168048 | | 11/2013 | |
| WO | WO 2013168048 | * | 11/2013 | ........... C07D 307/78 |
| WO | WO 2013/182264 | | 12/2013 | |

OTHER PUBLICATIONS

International Search Report, PCT/JP2015/079033, dated Dec. 15, 2015.
Okamoto,H. et al, Facile Synthesis of Picene from 1,2-Di(1-naphthyl )ethane by 9-FluorenoneSensitized Photolysis, Organic Letters, 2011, vol. 13, No. 10, pp. 2758-2761.
Mallory, F.B. et al, Phenacenes: a family of graphite ribbons. Part 3: Iterative strategies for the synthesis of large phenacenes, Tetrahedron, 2001, vol. 57, No. 17, pp. 3715-3724.
Wu,J. et al, New Angular-Shaped and Isomerically Pure Anthradithiophene with Lateral Aliphatic Side Chains for Conjugated Polymers: Synthesis, Characterization, and Implications for Solution-Prossessed Organic Field-Effect Transistors and Photovoltaics, Chemistry of Materials, 2012, vol. 24, No. 12, pp. 2391-2399.
Chen et al., "Regiocontrolled Synthesis of Ethene-Bridged. para-Phenylene Oligomers Based on PtII- and RuII-Catalyzed Aromatization", Chem Eur. J. 2010, 16, pp. 1826-1833.
Supplementary European Search Report dated Feb. 27, 2018 in corresponding European Patent Application No. 15853086.

* cited by examiner

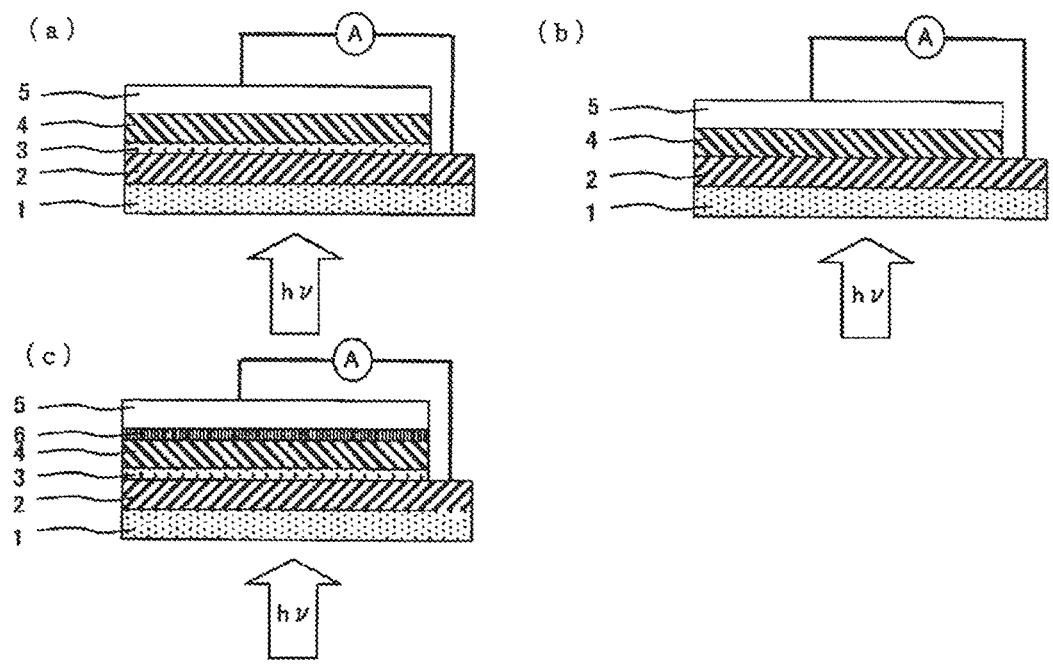

PICENE DERIVATIVE, PHOTOELECTRIC MATERIAL, AND PHOTOELECTRIC DEVICE

TECHNICAL FIELD

This invention relates to a noble p-type organic semiconductor material having a specific structure, a photoelectric material, and a photoelectric device using the same.

BACKGROUND ART

In recent years a solar cell (solar power generation) has been under intensive studies in view of sustainability, no involvement in the resource depletion problem, and environmental friendliness. Solar cells are roughly divided into inorganic solar cells including silicone-based and non-silicone-based solar cells and organic solar cells including dye-sensitized solar cells and organic thin film solar cells. Although inorganic solar cells generally achieve high photoelectric efficiency, they have the disadvantage of high production cost because of the necessity of high degree of vacuum and high-temperature heat treatment. Because organic solar cells, on the other hand, are fabricated by film formation by a solution process, or printing, they can be produced at a lower cost and with a larger effective area. Another advantage of organic solar cells is that they can be made lighter than inorganic solar cells. In particular, an organic thin-film solar cell is suitably fabricated by a printing technique that is applicable to a plastic film substrate and is regarded as easily capable of taking on the form of a flexible device.

However, organic solar cells often have low photoelectric efficiency, and the challenge is to increase the photoelectric efficiency.

A bulk heterojunction formed of a blend of poly(3-hexylthiophene) (P3HT) as a p-type organic semiconductor material and [6,6]-phenyl-C61-butyric acid methyl ester (PCBM) as an n-type organic semiconductor material has been so far proposed as a material that can achieve high photoelectric efficiency in organic thin-film solar cells (see non-patent Literature 1, etc. listed below). While a low-molecular compound, such as pentacene, is used in some cases, a polymer material is generally considered as suited to fabricate a solution-processed device, and it is believed that using a polymer material as a p-type organic semiconductor material makes it easier to hold down the cost and increase the effective area.

One of the characteristics demanded for a p-type organic semiconductor material is to contain a pi-conjugated system with high planarity. To have a highly planar pi-conjugated system in the material promises to benefit a strong pi-pi interaction and a high carrier transport efficiency and, as a result, provide high photovoltaic power.

Patent Literatures 1 to 3 below disclose techniques relating to p-type organic polymer semiconductor materials.

CITATION LIST

Patent Literature

Patent Literature 1: US 2008/0083455
Patent Literature 2: JP 2009/158921A
Patent Literature 3: JP 2011-116962A

Non-patent Literature

Non-patent Literature 1: F. Padinger, et al., *Adv. Funct. Mater.*, 13, 85 (2003)

SUMMARY OF THE INVENTION

Problem to be Solved by the Invention

An object of the invention is to provide a p-type organic semiconductor material that is easy to prepare and has high planarity in its polymer structure.

Another object of the invention is to provide a photoelectric layer, photoelectric device, and organic thin-film solar cell having high photoelectric efficiency by using the p-type organic semiconductor material.

Means to Solve the Problem

As a result of intensive investigations, the inventors have found that a picene derivative represented by general formula (1) is, when used as a p-type organic semiconductor material, capable of forming a photoelectric layer easily. The inventors' further study has led them to find that a photoelectric device having the photoelectric layer exhibits high carrier mobility and provides a solution to the above problem.

Based on the above findings, the invention provides a new picene derivative comprising at least one constitutional unit represented by general formula (1) (hereinafter referred to as: a picene derivative)

[Chem. 1]

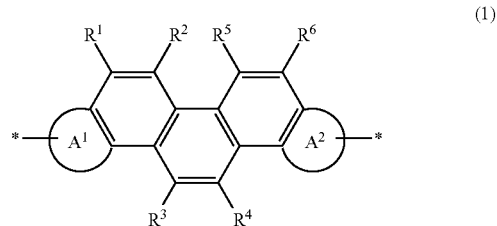

wherein $A^1$ and $A^2$ each independently represent a monocyclic ring; $R^1$, $R^2$, $R^3$, $R^4$, $R^5$, and $R^6$ each independently represent a hydrogen atom, a halogen atom, a cyano group, a nitro group, a hydroxy group, a carboxyl group, a thiol group, $-SiR^7R^8R^9$, $-NR^{10}R^{11}$, or an optionally substituted hydrocarbon group, provided that at least one of $R^1$, $R^2$, $R^3$, $R^4$, $R^5$, and $R^6$ is not hydrogen; and $R^7$, $R^8$, $R^9$, $R^{10}$, and $R^{11}$ each independently represent a hydrogen atom or an optionally substituted hydrocarbon group.

Also, the invention provides a photoelectric material comprising (A) the picene derivative as a p-type organic semiconductor material and (B) an n-type organic semiconductor material.

Also, the invention provides a photoelectric material comprising (A) a p-type organic semiconductor material including at least one picene derivative and (B) an n-type organic semiconductor material.

Also, the invention provides a photoelectric layer obtained by film formation using the photoelectric material.

Also, the invention provides a photoelectric device comprising the photoelectric layer.

Also, the invention provides an organic thin film solar cell comprising the photoelectric device.

Effect of the Invention

The invention provides a novel picene derivative useful as an organic semiconductor material. The use of the photoelectric material of the invention, which contains the compound, provides high carrier mobility and accomplishes enhancement of device performance.

BRIEF DESCRIPTION OF THE DRAWINGS

FIG. 1(a) is a cross-sectional view illustrating a structure of the photoelectric device of the invention.

FIG. 1(b) is a cross-sectional view illustrating another structure of the photoelectric device of the invention.

FIG. 1(c) is a cross-sectional view illustrating still another structure of the photoelectric device of the invention.

EMBODIMENTS FOR CARRYING OUT THE INVENTION

The picene derivative, photoelectric material, photoelectric layer, and organic thin-film solar cell according to the invention will be described on the basis of their preferred embodiments.

I. Picene Derivative

The picene derivative of the invention is a compound having at least one constitutional unit represented by general formula (1) shown above. The asterisk * in formula (1) indicates the position at which the constitutional unit is linked to an adjacent group (hereinafter the same).

The monocyclic ring represented by $A^1$ and $A^2$ in formula (1) is preferably, but not limited to, an aromatic monocyclic ring. Examples of the aromatic monocyclic ring include benzene, furan, thiophene, selenophene, tellurophene, thiazole, isothiazole, oxazole, isoxazole, pyridine, pyrazine, pyrimidine, pyridazine, pyrrole, imidazole, and pyrazole rings. Inter alia, a heterocyclic ring containing a sulfur, selenium, or tellurium atom is preferred for the improvement of device characteristics.

In formula (1) $R^1$, $R^2$, $R^3$, $R^4$, $R^5$, and $R^6$ each independently represent a hydrogen atom, a halogen atom, a cyano group, a nitro group, a hydroxy group, a carboxyl group, a thiol group, $-SiR^7R^8R^9$, $-NR^{10}R^{11}$, or an optionally substituted hydrocarbon group, provided that at least one of them is not hydrogen, wherein $R^7$, $R^8$, $R^9$, $R^{10}$, and $R^{11}$ each independently represent a hydrogen atom or an optionally substituted hydrocarbon group.

Examples of the halogen atom in formula (1) include fluorine, chlorine, bromine, and iodine.

Examples of the hydrocarbon group in formula (1) include aromatic hydrocarbon groups, aromatic hydrocarbon groups substituted with an aliphatic hydrocarbon group, and aliphatic hydrocarbon groups. The hydrocarbon group preferably contains 1 to 40, more preferably 4 to 22, carbon atoms.

Examples of the aromatic hydrocarbon group include phenyl, naphthyl, cyclohexylphenyl, biphenyl, terphenyl, fluorenyl, thiophenylphenyl, furanylphenyl, 2'-phenyl-propylphenyl, benzyl, and naphthylmethyl.

Examples of the aliphatic hydrocarbon group include straight-chain, branched, or cyclic alkyl groups, such as methyl, ethyl, propyl, isopropyl, butyl, s-butyl, t-butyl, isobutyl, amyl, isoamyl, t-amyl, hexyl, heptyl, isoheptyl, t-heptyl, n-octyl, isooctyl, t-octyl, nonyl, cyclopropyl, cyclobutyl, cyclopentyl, cyclohexyl, cycloheptyl, cyclooctyl, cyclononyl, and cyclodecyl. The aliphatic hydrocarbon group may be interrupted by $-O-$, $-COO-$, $-OCO-$, $-CO-$, $-S-$, $-SO-$, $-SO_2-$, $-NR^{15}$, $-HC=CH-$, or $-C\equiv C-$. The interrupting group may interrupt the bond at which the aliphatic hydrocarbon group is bonded. The symbol $R^{15}$ represents an optionally substituted hydrocarbon group, examples of which include those recited above. $R^{15}$ is preferably perfluoroalkyl.

Examples of the aromatic hydrocarbon group substituted with an aliphatic hydrocarbon group include phenyl, naphthyl, and benzyl each substituted with any of the above described aliphatic hydrocarbon groups.

Examples of the substituent that may be bonded to the hydrocarbon groups include a halogen atom, a cyano group, a nitro group, a hydroxy group, a carboxyl group, a thiol group, and $-NR'R''$ wherein R' and R'' each represent an optionally substituted hydrocarbon group, the examples of which include those recited above.

Of the picene derivatives preferred are those having 2 to 100 constitutional units represented by general formula (1) for their excellent film-forming properties. The picene derivative may have a constitutional unit other than the one represented by formula (1) (hereinafter referred to as other constitutional unit). When the picene derivative contains other constitutional unit(s), the ratio of the constitutional unit of the formula (1) is preferably 5 to 100 mol %, more preferably 10 to 90 mol %, even more preferably 20 to 80 mol %.

Of the picene derivatives of formula (1) preferred are those represented by general formula (1-1) or (1-2) shown below for ease of preparation.

[Chem. 2]

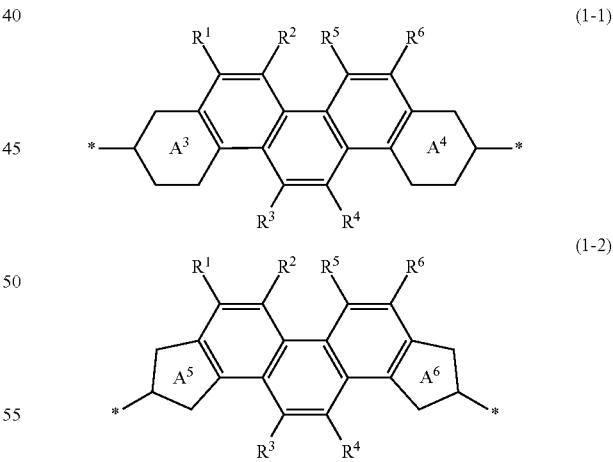

wherein $A^3$ and $A^4$ each represent a 6-membered ring selected from the examples of the monocyclic ring represented by $A^1$ and $A^2$; $A^5$ and $A^6$ each represent a 5-membered ring selected from the examples of the monocyclic ring represented by $A^1$ and $A^2$; $R^1$, $R^2$, $R^3$, $R^4$, $R^5$, and $R^6$ are as defined with respect to formula (1), provided that at least one of $R^1$, $R^2$, $R^3$, $R^4$, $R^5$, and $R^6$ is not hydrogen.

Of the picene derivatives of formulae (1-1) and (1-2) preferred in terms of ease of preparation are those of formula (1-1) in which $A^3$ and $A^4$ are the same 6-membered ring and those of formula (1-2) in which $A^5$ and $A^6$ are the same 5-membered ring.

The other constitutional unit is not particularly limited as long as it is a pi-conjugated group. Examples of the other constitutional unit include those of group Y and group Z shown below. The constitutional units (Y-2), (Y-3), and (Y-4) and constitutional units selected from group Z are preferred in the interests of material durability and light resistance.

[Chem. 3]
<Group Y>

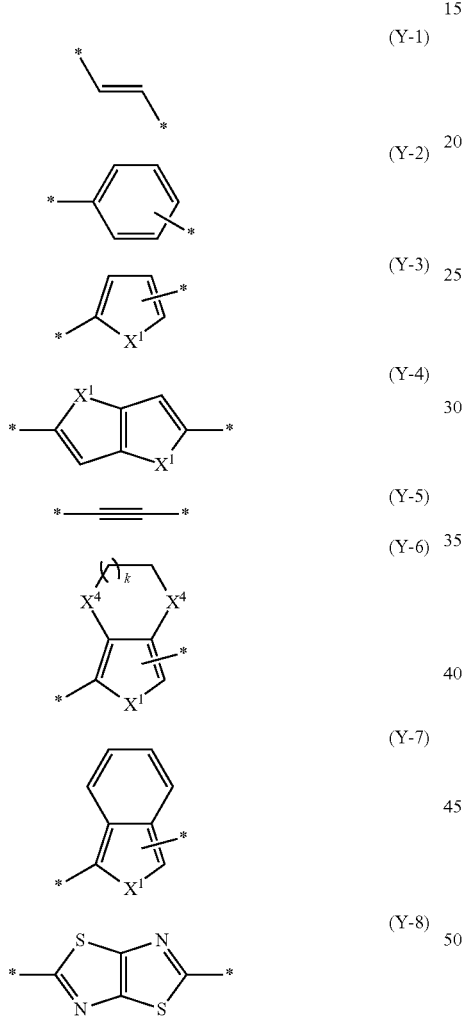

wherein $X^1$ and $X^4$ each represent S, O, or $NR^{12}$; k represents an integer of 1 to 4; $R^{12}$ represents an optionally substituted hydrocarbon group; the hydrogen atom of the constitutional units of group Y is optionally replaced with a halogen atom, a cyano group, a nitro group, a hydroxy group, a carboxyl group, a thiol group, $-NR^{13}R^{14}$, an optionally substituted hydrocarbon group, or an optionally substituted heterocyclic group; and $R^{13}$ and $R^{14}$ each represent an optionally substituted hydrocarbon group.

[Chem. 4]
<Group Z>

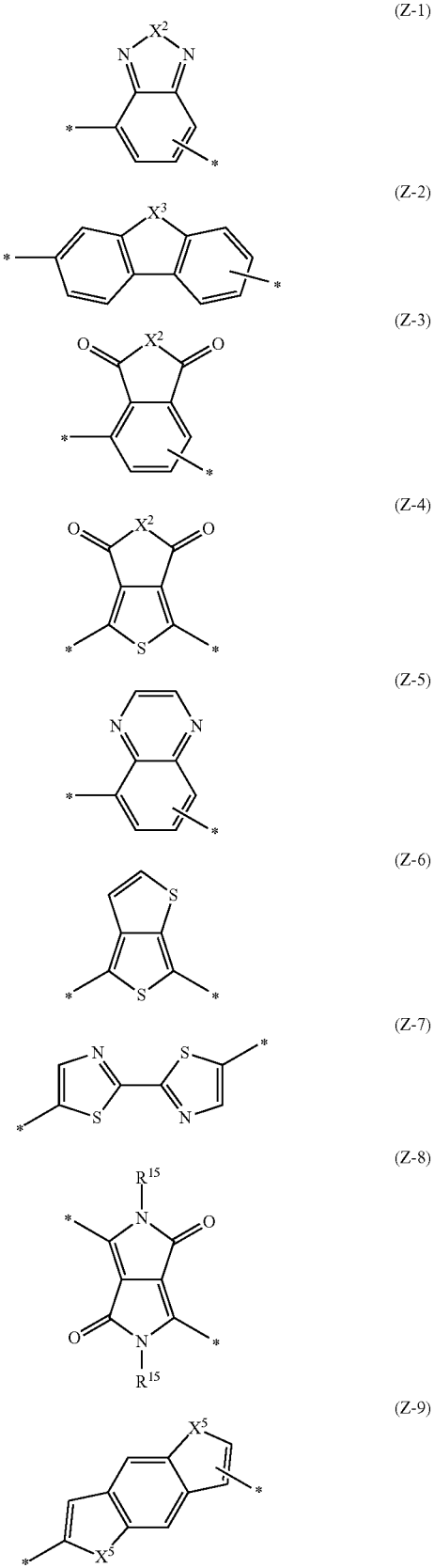

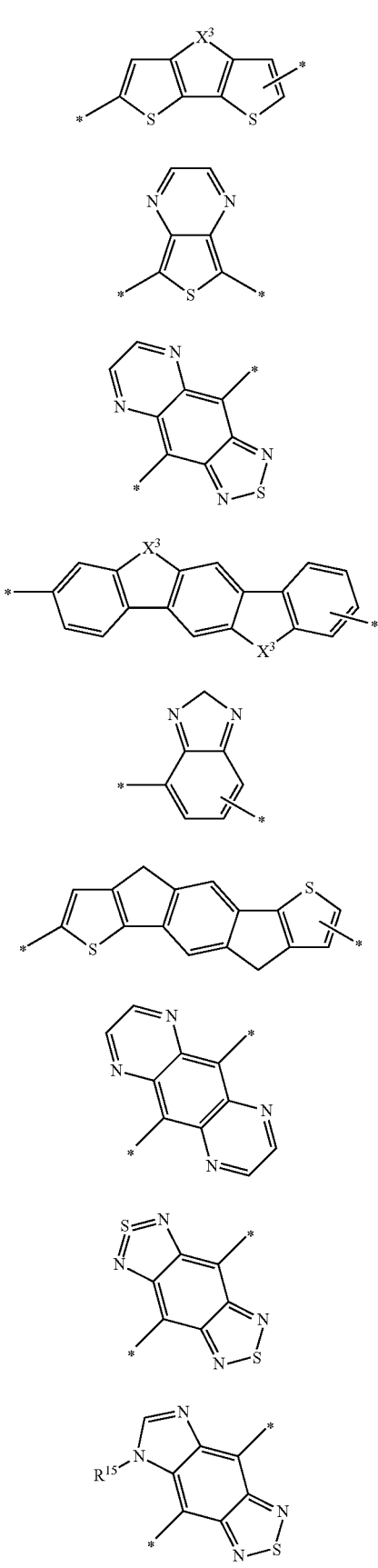

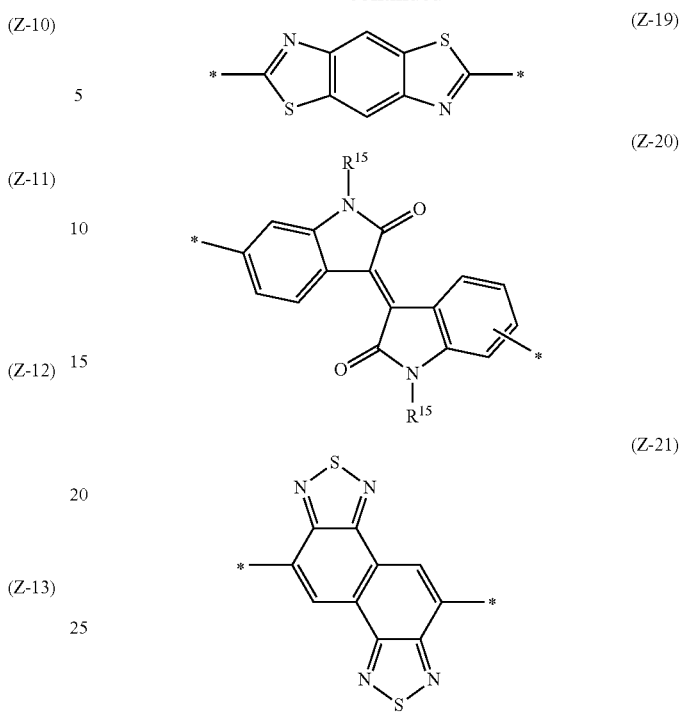

wherein $X^2$ represents S or $NR^{15}$; $X^3$ represents S, $NR^{15}$, $CR^{16}R^{17}$, or $SiR^{16}R^{17}$; $X^5$ represents S, O, or $NR^{15}$; $R^{15}$, $R^{16}$, and $R^{17}$ each represent an optionally substituted hydrocarbon group; the hydrogen atom of the constitutional units of group Z is optionally replaced with a halogen atom, a cyano group, a nitro group, a hydroxy group, a carboxyl group, a thiol group, $-NR^{18}R^{19}$, an optionally substituted hydrocarbon group, or an optionally substituted heterocyclic group; and $R^{18}$ and $R^{19}$ each represent an optionally substituted hydrocarbon group.

Examples of the hydrocarbon group that may replace the hydrogen atom of the constitutional units included in groups Y and Z and the optionally substituted hydrocarbon group as represented by $R^{12}$ (of $NR^{12}$ represented by $X^1$ and $X^4$ in group Y), $R^{15}$ (in group Z and of $NR^{15}$ as represented by $X^2$ and $X^5$ and of $NR^{15}$ as represented by $X^3$ in group Z), and $R^{16}$ and $R^{17}$ (of $CR^{16}R^{17}$ and $SiR^{16}R^{17}$ as represented by $X^3$ in group Z) are the same as those of the optionally substituted hydrocarbon group in formula (1).

In the case when the picene derivative contains the constitutional unit selected from groups Y and Z, the picene derivative is represented by general formula (1') shown below. The sequence of the o, p, and q constitutional units is not particularly restricted, and the effects of the invention are produced irrespective of the sequence. As for the ratios of the constitutional units, when the number o of the constitutional unit of formula (1) is taken as 1, the number p of the constitutional units of group Y and the number q of the constitutional units of group Z are each preferably 1 to 10. The number p is more preferably 0 to 8, even more preferably 1 to 5, in the interests of light absorption efficiency in a long wavelength region. The number q is more preferably 0 to 2, even more preferably 1 to 2, most preferably 1, in view of light absorption efficiency in a long wavelength region.

[Chem.5]

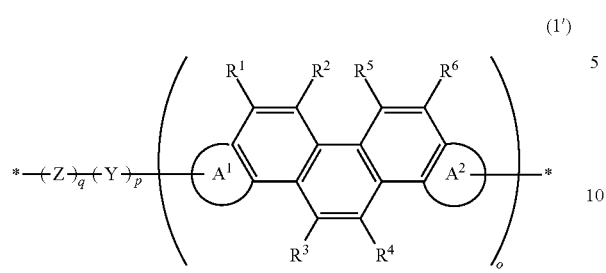
(1')

wherein the hydrogen atom may be replaced similarly to the formula (1); Y represents a group selected from group Y; Z represents a group selected from group Z: o is a number of 1 to 1000; and p and q are each a number of 0 to 1000.

Preferred examples of the picene derivative are compounds represented by general formula (2) below, particularly compounds represented by general formula (2-1) or (2-2):

[Chem. 6]

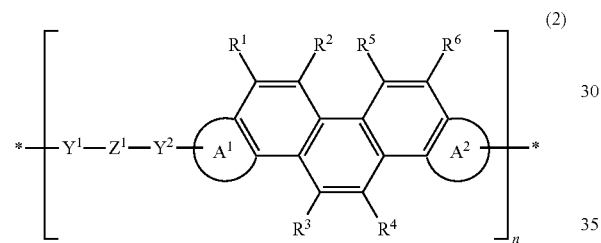
(2)

wherein $A^1$, $A^2$, $R^1$, $R^2$, $R^3$, $R^4$, $R^5$, and $R^6$ are as defined above with respect to formula (1); at least one $R^1$, $R^2$, $R^3$, $R^4$, $R^5$, and $R^6$ is not hydrogen; $Y^1$ and $Y^2$ each represent a single bond or a combination of 1 to 5 groups selected from (Y-1) to (Y-8) below linked to each other; $Z^1$ represents a single bond or a group selected form (Z-1) to (Z-21) below; and n represents an integer of 1 to 1000.

[Chem. 7]

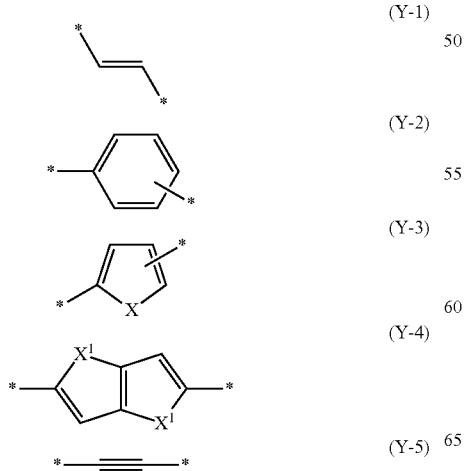

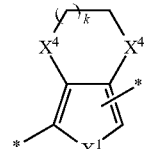
(Y-6)

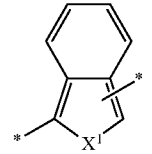
(Y-7)

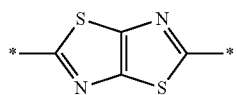
(Y-8)

wherein $X^1$ and $X^4$ each represent S, O, or $NR^{12}$; k represents an integer 1 to 4; $R^{12}$ represents an optionally substituted hydrocarbon group; the hydrogen atom of the groups (Y-1) to (Y-4) and (Y-6) to (Y-8) is optionally replaced with a halogen atom, a cyano group, a nitro group, a hydroxy group, a carboxyl group, a thiol group, $-NR^{13}R^{14}$, an optionally substituted hydrocarbon group, or an optionally substituted heterocyclic group; and $R^{13}$ and $R^{14}$ each represent an optionally substituted hydrocarbon group.

[Chem.8]

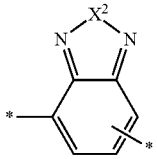
(Z-1)

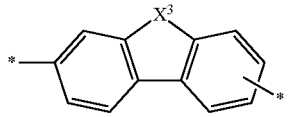
(Z-2)

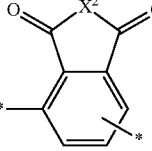
(Z-3)

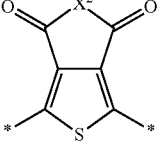
(Z-4)

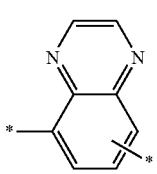
(Z-5)

-continued

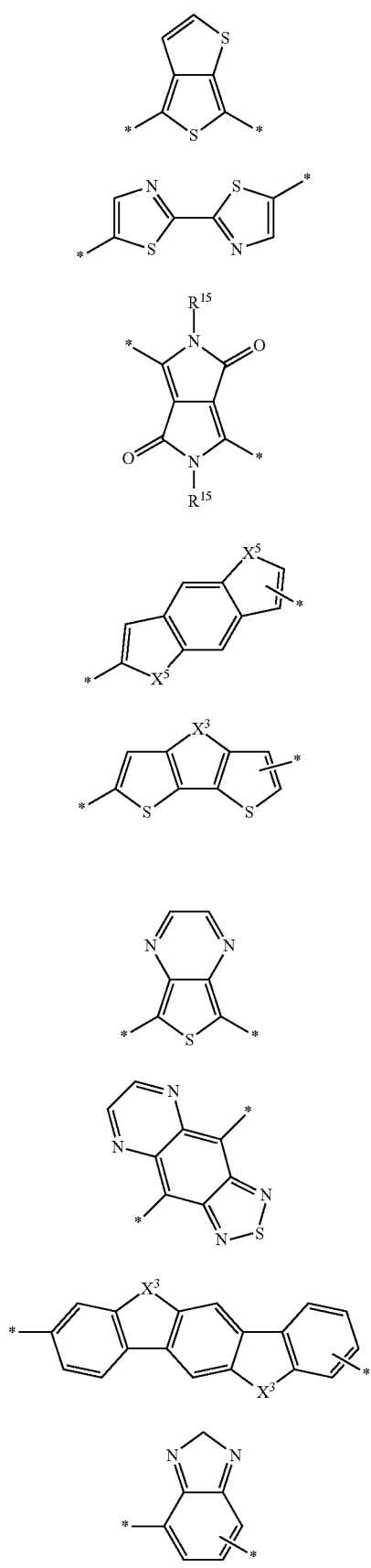

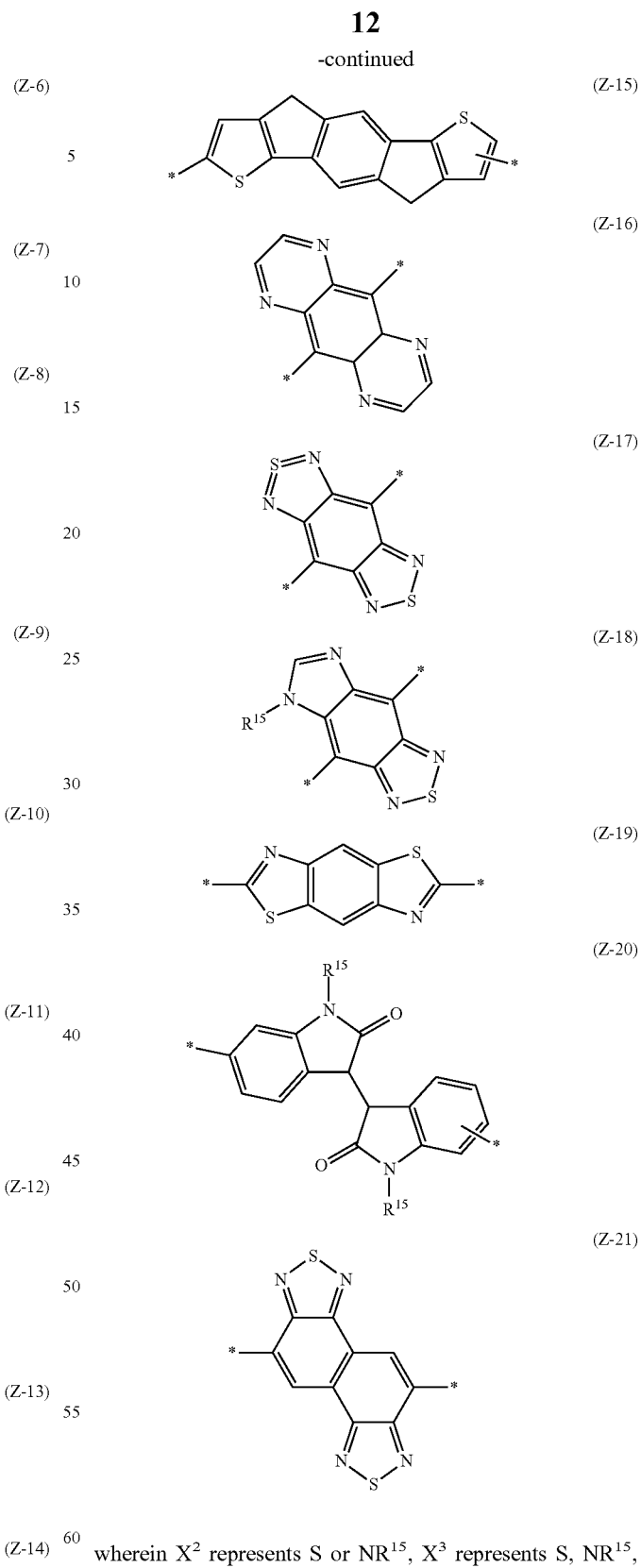

wherein $X^2$ represents S or $NR^{15}$, $X^3$ represents S, $NR^{15}$, $CR^{16}R^{17}$, or $SiR^{16}R^{17}$; $X^5$ represents S, O, or $NR^{15}$; $R^{15}$, $R^{16}$, and $R^{17}$ each represent an optionally substituted hydrocarbon group; the hydrogen atom of the groups (Z-1) to (Z-21) is optionally replaced with a halogen atom, a cyano group, a nitro group, a hydroxy group, a carboxyl group, a thiol group, —$NR^{18}R^{19}$, an optionally substituted hydrocarbon group, or an optionally substituted heterocyclic group; and R¹⁸ and R¹⁹ each represent an optionally substituted hydrocarbon group.

[Chem. 8A]

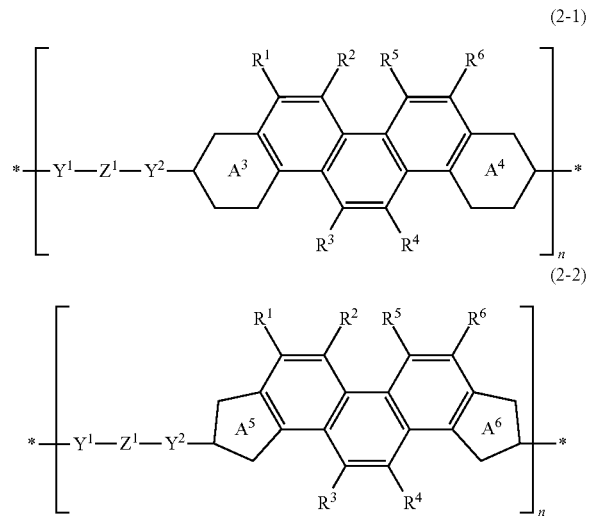

wherein A¹, A², R¹, R², R³, R⁴, R⁵, and R⁶ are as defined above with respect to formula (1); A³ and A⁴ are as defined with respect to formula (1-1); A⁵ and A⁶ are as defined with respect to formula (1-2); Y¹, Y², Z¹, and n are as defined with respect to formula (2); and at least one of R¹, R², R³, R⁴, R⁵, and R⁶ is not hydrogen.

Of the compounds of formulae (2), (2-1), and (2-2) preferred are those in which at least one of Y¹, Y², and Z¹ is not a single bond for their excellent characteristics demanded for a photoelectric device.

In the compounds of formulae (2), (2-1), and (2-2) at least one of R¹, R², R³, R⁴, R⁵, and R⁶ is a substituent (≠H). While the effects of the invention are produced irrespective of the selection of the substituent R¹, R², R³, R⁴, R⁵, or R⁶, it is preferred that at least one of R¹, R², R³, R⁴, R⁵, and R⁶ be C1-C30 unsubstituted alkyl or C1-C30 substituted alkyl, the methylene moiety of the substituted or unsubstituted alkyl may be —CH=CH— or the substituent on the alkyl group being selected from alkoxy, alkylthio, aryl, aryloxy, arylthio, heterocyclic group, acyl, acyloxy, amino, sulfonyl, carboxyl, cyano, sulfo, hydroxy, mercapto, imido, and halogen. It is more preferred that at least one of R¹, R², R³, R⁴, R⁵, and R⁶ be C1-C30 unsubstituted alkyl or C1-C30 substituted alkyl, particularly C10-C20 substituted or unsubstituted alkyl.

While the effects of the invention are obtained irrespective of which of R¹, R², R³, R⁴, R⁵, and R⁶ is a substituent H), it is preferred that R¹, R³, R⁴, and R⁶ be a substituent, more preferably R¹ and R⁶ be a substituent.

Specific examples of the picene derivative include, but are not limited to, compound Nos. 1 through 17 shown below. In formulae below R¹, R², R³, R⁴, R⁵, and R⁶ are as defined with respect to formula (1); n is as defined with respect to formula (2); Hex represents hexyl; 2-EH represents 2-ethylhexyl; 2-HD represents 2-hexyldecyl; and 2-OD represents 2-octyldodecyl.

[Chem.9]

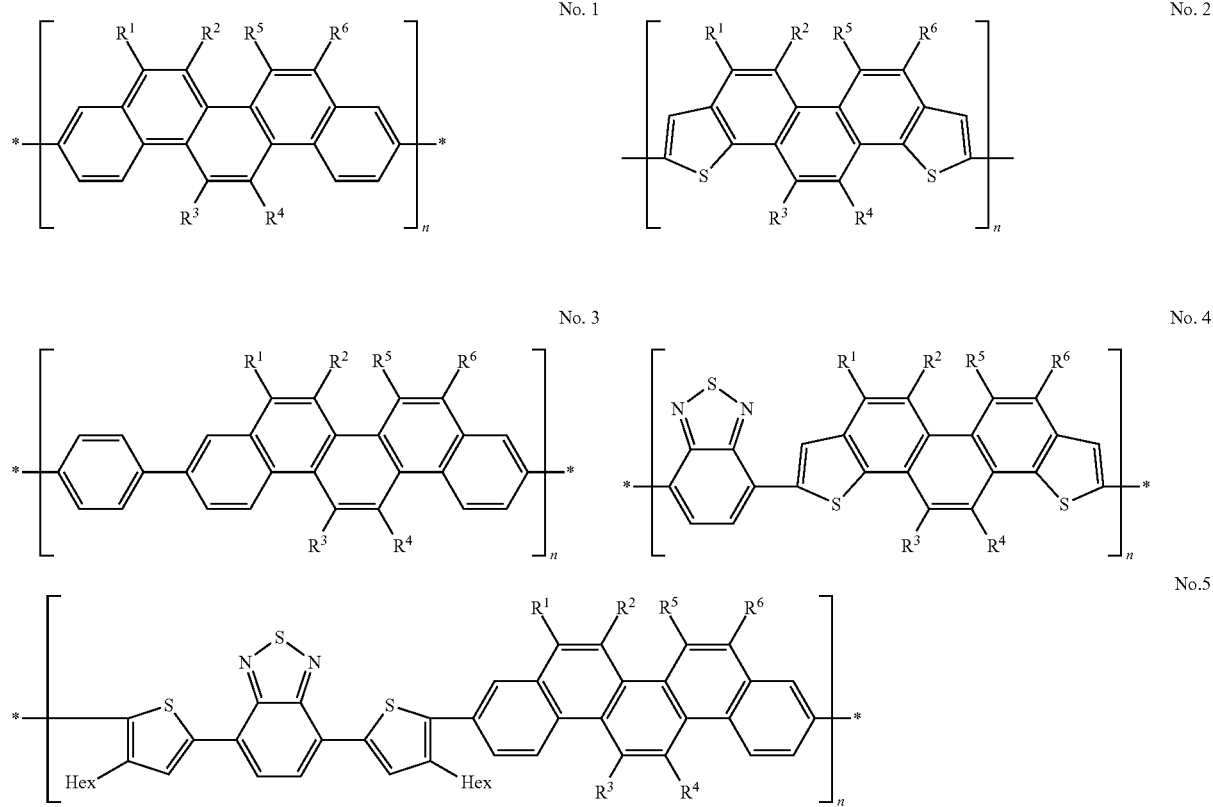

-continued
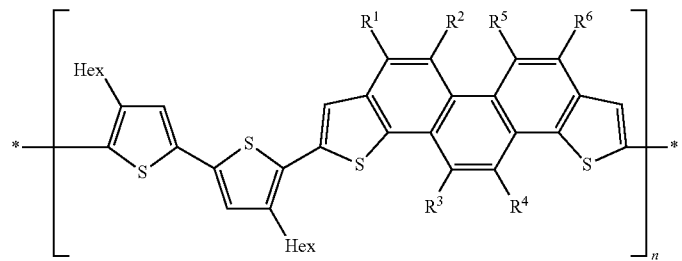
No. 6
[Chem.10]
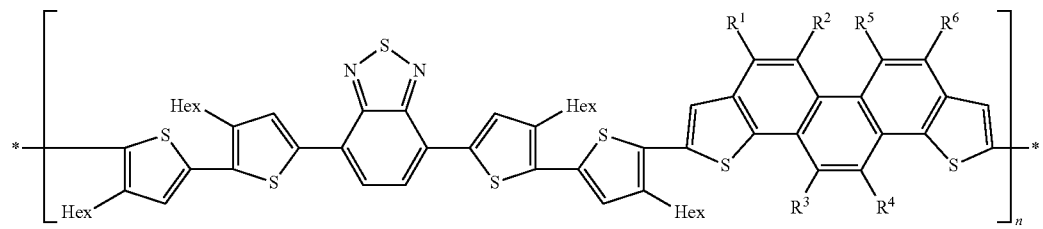
No. 7
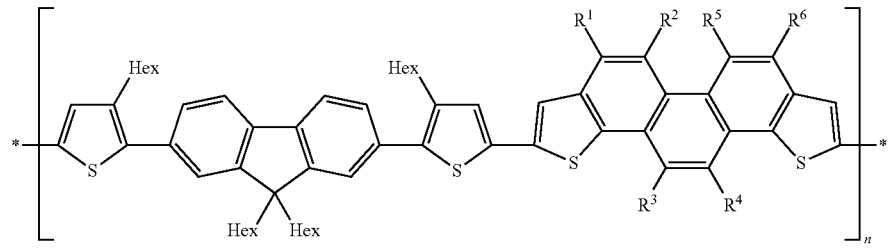
No. 8
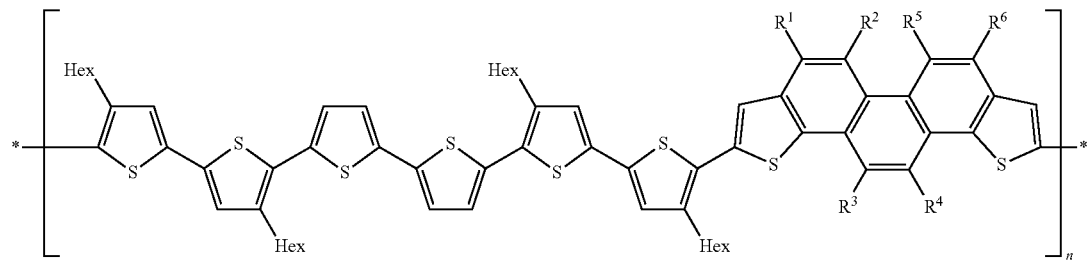
No. 9
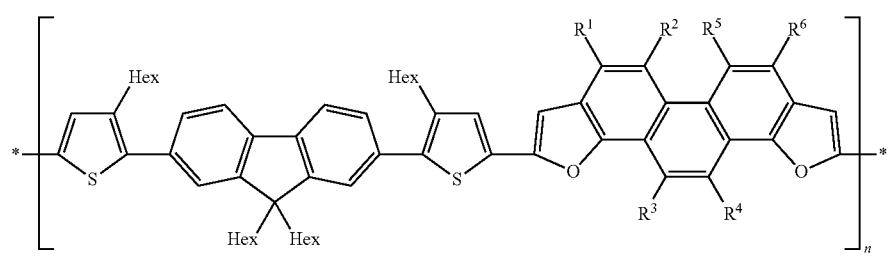
No. 10
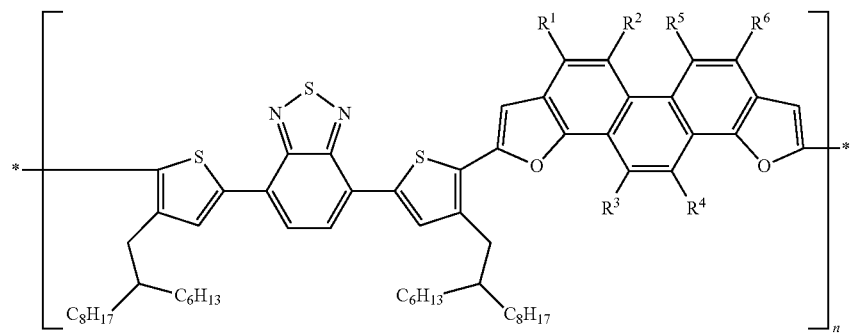
No. 11

-continued
[Chem.11]
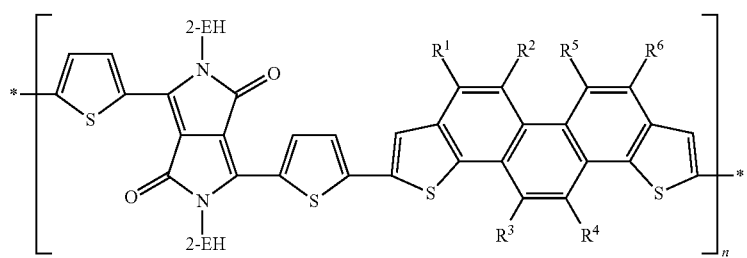
No. 12
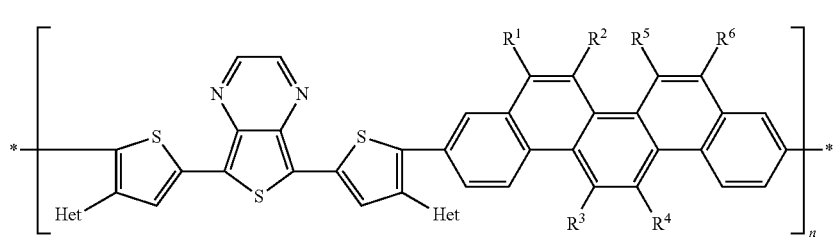
No. 13
No. 14
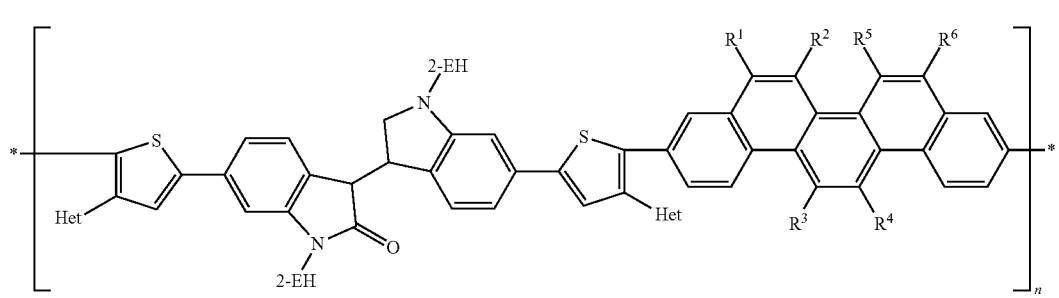
No. 15

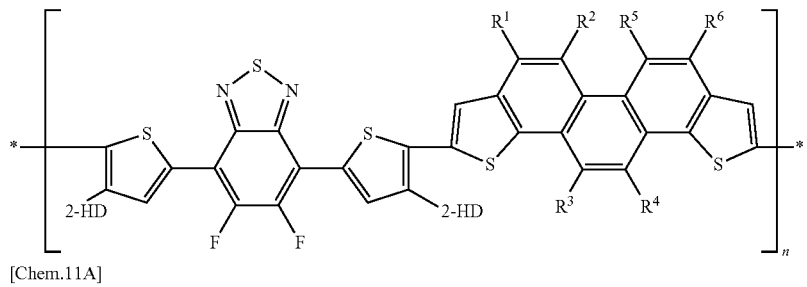

[Chem.11A]

No. 16

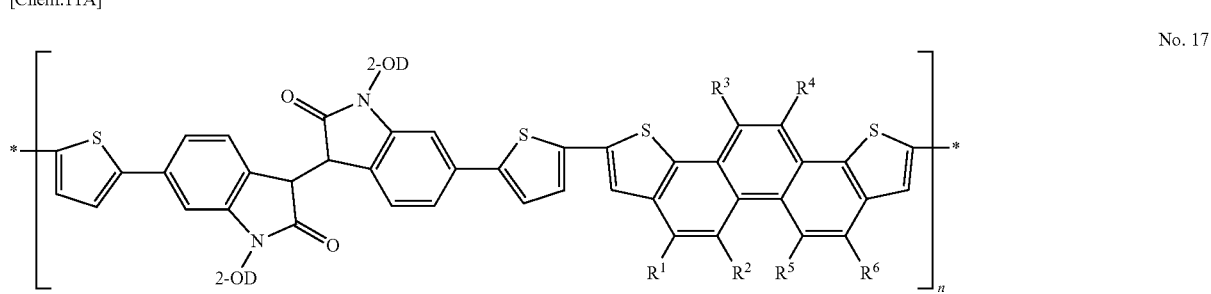

No. 17

The picene derivative of the invention may be prepared by any method making use of commonly known reactions. For example, the picene derivative of formula (2) can be prepared by polycondensation reaction between a bistrimethyltin compound (4) derived from a starting picene derivative (3) and a halogenated pi-conjugated compound (5) obtained by a known synthesis method in accordance with the following reaction scheme:

[Chem.12]

Reaction Scheme:

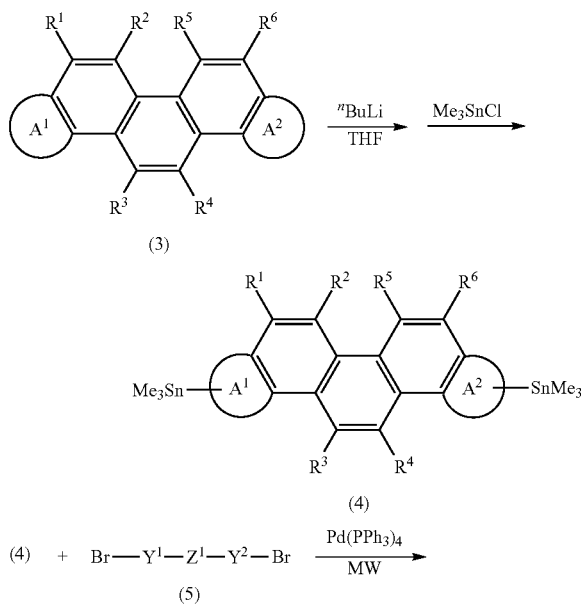

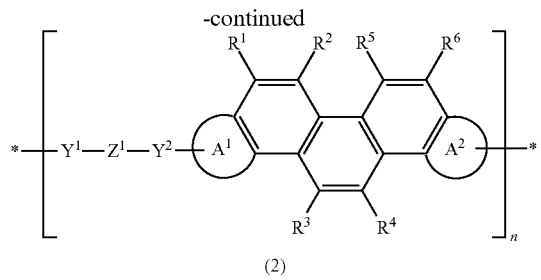

(2)

wherein $A^1$, $A^2$, $R^1$, $R^2$, $R^3$, $R^4$, $R^5$, $R^6$, $Y^1$, $Y^2$, $Z^1$, and n are as defined with respect to formula (2).

The picene derivative of the invention is suited not only as an organic semiconductor material but also for other uses, such as an antioxidant.

II. Photoelectric Material

The photoelectric material of the invention contains (A) a p-type organic semiconductor material containing at least one picene derivative of the invention and (B) an n-type organic semiconductor material.

The p-type organic semiconductor material (A), which should contain at least one picene derivative of the invention, may further contain other known materials. The above description of the picene derivative applies appropriately to the picene derivative to be used in the photoelectric material. Examples of the known materials include phthalocyanine pigments, indigo or thioindigo pigments, quinacridone pigments, triarylmethane derivatives, triarylamines derivatives, oxazole derivatives, hydrazine derivatives, stilbene derivatives, pyrazoline derivatives, polysilane derivatives, polyphenylenevinylene and its derivatives (e.g., poly[2-methoxy-5-(2-ethylhexyloxy)-1,4-phenylenevinylene] (MEH-PPV) and poly[2-methoxy-5-(3',7'-dimethyloctyloxy)-1,4-phenylenevinylene]), polythiophene and its derivatives (e.g., poly(3-dodecylthiophene), poly(3-hexylthiophene) (P3HT), and poly(3-octylthiophene)), and poly-N-vinylcarbazole derivatives.

In the case when the p-type organic semiconductor material (A) contains the known material, the picene derivative content in the p-type organic semiconductor material (A) is preferably 1 to 99 mass %, more preferably 1 to 80 mass %.

Examples of useful n-type organic semiconductor materials (B) include perylene pigments, perinone pigments, polycyclic quinone pigments, azo pigments, and fullerene C60 or C70 and their derivatives. Additionally included are organic metal complexes (e.g., tris(8-quinolinolato)aluminum, bis(10-benzo[h]quinolinolato)beryllium, 5-hydroxyflavone beryllium salt, and 5-hydroxyflavone aluminum salt), oxadiazole derivatives (e.g., 1,3-bis[5'-(p-t-butylphenyl)-1,3,4-oxadiazol-2'-yl]benzene), triazole derivatives (e.g., 3-(4'-t-butylphenyl)-4-phenyl-5-(4"-biphenyl)-1,2,4-triazole), phenanthroline derivatives (e.g., 2,9-dimethyl-4,7-diphenyl-1,10-phenanthroline (bathocuproine or BCP), triazine derivatives, quinoline derivatives, quinoxaline derivatives, diphenylquinone derivatives, nitro-substituted fluorenone derivatives, and thiopyran dioxide derivatives. Of the n-type organic semiconductor materials (B) described above preferred are fullerene C60, fullerene C70, and their derivatives for their high carrier mobility and/or high charge separation efficiency as an n-type material. The compounds listed above as an n-type organic semiconductor material may be used either individually or in combination of two or more thereof.

Examples of fullerene C60, fullerene C70 or their derivatives include compounds C1 to C6 shown below. Preferred of them is compound C1, i.e., phenyl-C61-butyric acid methyl ester (PCBM).

[Chem. 13]

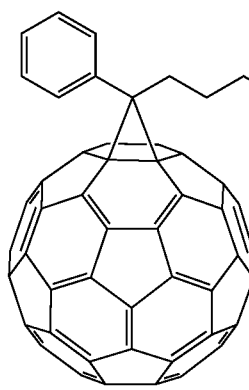

PCBM
C1

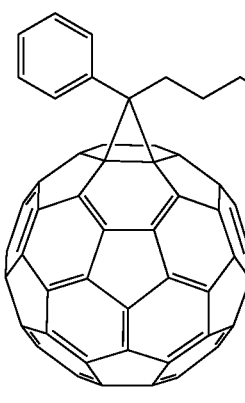

PCBB
C2

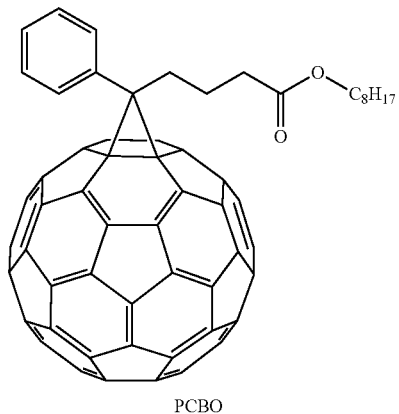

PCBO
C3

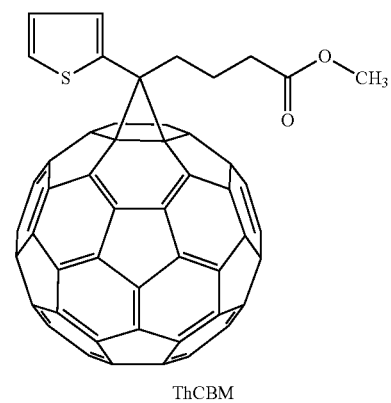

ThCBM
C4

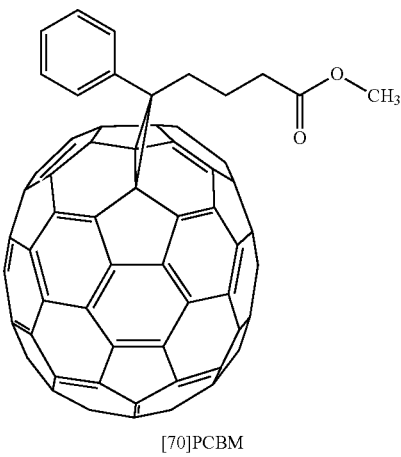

[70]PCBM
C5

C6

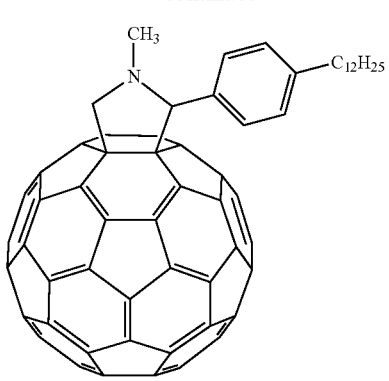

The weight ratio of component (A) to component (B) in the photoelectric material of the invention is 10:90 to 90:10, preferably 10:90 to 70:30, more preferably 20:80 to 50:50.

Where needed, the photoelectric material of the invention may contain one or more solvents.

Any solvent capable of dissolving or dispersing components (A) and (B) may be used. Examples of useful solvents include water, alcohols, diols, ketones, esters, ethers, aliphatic or alicyclic hydrocarbons, aromatic hydrocarbons, cyano-containing hydrocarbons, halogenated hydrocarbons, and others. A photoelectric material containing a solvent is useful as a coating solution.

Examples of the alcohols include methanol, ethanol, propanol, isopropyl alcohol, 1-butanol, isobutanol, 2-butanol, t-butanol, pentanol, isopentanol, 2-pentanol, neopentanol, t-pentanol, hexanol, 2-hexanol, heptanol, 2-heptanol, octanol, 2-ethylhexanol, 2-octanol, cyclopentanol, cyclohexanol, cycloheptanol, methylcyclopentanol, methylcyclohexanol, methylcycloheptanol, benzyl alcohol, ethylene glycol monomethyl ether, ethylene glycol monoethyl ether, propylene glycol monomethyl ether, propylene glycol monoethyl ether, diethylene glycol monomethyl ether, diethylene glycol monoethyl ether, triethylene glycol monomethyl ether, triethylene glycol monoethyl ether, 2-(N,N-dimethylamino)ethanol, and 3-(N,N-dimethylamino)propanol.

Examples of the diols include ethylene glycol, propylene glycol, 1,2-butanediol, 1,3-butanediol, 1,4-butanediol, 1,5-pentanediol, neopentyl glycol, isoprene glycol (3-methyl-1,3-buanediol), 1,2-hexanediol, 1,6-hexanediol, 3-methyl-1,5-pentanediol, 1,2-octanediol, octanediol (2-ethyl-1,3-hexanediol), 2-butyl-2-ethyl-1,3-propanediol, 2,5-dimethyl-2,5-hexanediol, 1,2-cyclohexanediol, 1,4-cyclohexanediol, and 1,4-cyclohexanedimethanol.

Examples of the ketones include acetone, ethyl methyl ketone, methyl isopropyl ketone, methyl butyl ketone, methyl isobutyl ketone, methyl amyl ketone, methyl hexyl ketone, ethyl butyl ketone, diethyl ketone, dipropyl ketone, diisobutyl ketone, methyl amyl ketone, cyclohexanone, and methylcyclohexanone.

Examples of the esters include methyl formate, ethyl formate, methyl acetate, ethyl acetate, isopropyl acetate, butyl acetate, isobutyl acetate, s-butyl acetate, t-butyl acetate, amyl acetate, isoamyl acetate, t-amyl acetate, phenyl acetate, methyl propionate, ethyl propionate, isopropyl propionate, butyl propionate, isobutyl propionate, s-butyl propionate, t-butyl propionate, amyl propionate, isoamyl propionate, t-amyl propionate, phenyl propionate, methyl 2-ethylhexanoate, ethyl 2-ethylhexanolate, propyl 2-ethylhexanoate, isopropyl 2-ethylhexanoate, butyl 2-ethylhexanoate, methyl lactate, ethyl lactate, methyl methoxypropionate, methyl ethoxypropionate, ethyl methoxypropionate, ethyl ethoxypropionate, ethylene glycol monomethyl ether acetate, diethylene glycol monomethyl ether acetate, ethylene glycol monoethyl ether acetate, ethylene glycol monoethyl ether acetate, ethylene glycol monopropyl ether acetate, ethylene glycol monoisopropyl ether acetate, ethylene glycol monobutyl ether acetate, ethylene glycol mono-s-butyl ether acetate, ethylene glycol monoisobutyl ether acetate, ethylene glycol mono-t-butyl ether acetate, propylene glycol monomethyl ether acetate, propylene glycol monoethyl ether acetate, propylene glycol monopropyl ether acetate, propylene glycol monoisopropyl ether acetate, propylene glycol monobutyl ether acetate, propylene glycol mono-s-butyl ether acetate, propylene glycol monoisobutyl ether acetate, propylene glycol mono-t-butyl ether acetate, butylene glycol monomethyl ether acetate, butylene glycol monoethyl ether acetate, butylene glycol monopropyl ether acetate, butylene glycol monoisopropyl ether acetate, butylene glycol monobutyl ether acetate, butylene glycol mono-s-butyl ether acetate, butylene glycol monoisobutyl ether acetate, butylene glycol mono-t-butyl ether acetate, methyl acetoacetate, ethyl acetoacetate, methyl oxobutanoate, ethyl oxobutanoate, γ-lactone, dimethyl malonate, dimethyl succinate, propylene glycol diacetate, and δ-lactone.

Examples of the ethers include tetrahydrofuran, tetrahydropyran, morpholine, ethylene glycol dimethyl ether, diethylene glycol dimethyl ether, dipropylene glycol dimethyl ether, triethylene glycol dimethyl ether, dibutyl ether, diethyl ether, and dioxane.

Examples of the aliphatic or alicyclic hydrocarbons include pentane, hexane, cyclohexane, methylcyclohexane, dimethylcyclohexane, ethylcyclohexane, heptane, octane, decaline, solvent naphtha, terpene oil, D-limonene, pinene, mineral spirit, Swasol 310 (from Cosmo Oil), and Solvesso 100 (from Exxon Chemical).

Examples of the aromatic hydrocarbons include benzene, toluene, ethylbenzene, xylene, mesitylene, diethylbenzene, cumene, isobutylbenzene, cymene, and tetralin.

Examples of the cyano-containing hydrocarbons include acetonitrile, 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene.

Examples of the halogenated hydrocarbons include carbon tetrachloride, chloroform, trichloroethylene, chlorobenzene, dichlorobenzene, and trichlorobenzene.

The other organic solvents include N-methyl-2-pyrrolidone, dimethyl sulfoxide, dimethylformamide, aniline, triethylamine, pyridine, and carbon disulfide.

Of these organic solvents preferred are chloroform, dichloromethane, toluene, xylene, chlorobenzene, dichlorobenzene, and trichlorobenzene.

The content of the organic solvent in the photoelectric material of the invention is not particularly limited as long as the photoelectric material is capable of forming a photoelectric layer. A preferred solvent content is such that the total amount of components (A) and (B) in the photoelectric material may range from 0.1 to 20 parts by weight, more preferably 1 to 10 parts by weight, even more preferably 3 to 7 parts by weight, per 100 parts by weight of the solvent.

III. Photoelectric Layer

The photoelectric layer of the invention will next be described. The photoelectric layer of the invention is obtained by film formation techniques using the photoelectric material of the invention. Film formation techniques for forming a coating film on a substrate include, but are not limited to, dry processes, such as vapor deposition, physical vapor growth (PVD), chemical vapor growth (CVD), atomic layer deposition (ALD), atomic layer epitaxy (ALE), molecular beam epitaxy (MBE), vapor phase epitaxy (VPE), sputtering, and plasma polymerization; and wet processes, such as dip coating, casting, air knife coating, curtain coating, roller coating, wire bar coating, gravure coating, spin coating, LB process, offset printing, screen printing, flexography, dispenser printing, ink jet printing, and extrusion coating.

The thickness of the photoelectric layer is usually preferably, but not limited to, about 5 nm to 5 μm. The layer may be subjected to a heat treatment, such as annealing.

The photoelectric layer is used in devices in which a blend of a p-type and an n-type organic semiconductor material is used, including not only organic bulk heterojunction devices, which are preferred embodiments, but super-hierarchical nanostructure junction devices, hybrid heterojunction devices, and the i-type layer of p-i-n junction devices.

IV. Photoelectric Device and Organic Thin Film Solar Cell

The photoelectric device of the invention is structurally equal to conventionally known photoelectric devices, except for containing at least one photoelectric layer of the invention. Taking, for instance, the structure shown in FIG. 1(a), it has a support 1, an electrode 2, a charge transfer layer 3, a photoelectric layer 4, and an electrode 5 stacked in the order described. The photoelectric device may have a structure having no charge transfer layer 3 as illustrated in FIG. 1(b) or a structure having an additional charge transfer layer 6 as illustrated in FIG. 1(c).

The photoelectric device of the invention should transmit light from the side of the support 1 to the photoelectric layer 4. In order to allow incident light to reach the photoelectric layer 4 through the support 1, the electrode 2, and the charge transfer layer 3, it is preferred that the support 1, the electrode 2, and the charge transfer layer 3 be made of a light transmissive material and have a transmittance of at least 70%.

The support 1 is not limited by material and thickness as long as it is capable of stably supporting the electrode 2 on its surface but should be transparent. The support may be a plate or a film. As used herein, the term "transparent" means capable of transmitting light of a predetermined wavelength region used for photoelectric devices, for example, visible light at high transmittances. Examples of the support 1 include glass and transparent film of polymers, such as polyethylene terephthalate (PET), tetraacetyl cellulose (TAC), polycarbonate, polyethylene naphthalate, polyphenylene sulfide, polyester sulfone, and syndiotactic polystyrene. While the photoelectric device of the invention is preferably fabricated on the surface of the support 1, the electrode 2 may be configured to double as the support 1 when the electrode 2 itself is a self-supporting layer with certain hardness. In such a case, the support 1 may be omitted.

The mutually facing electrodes (electrodes 2 and 5) are related to each other such that the work function of one of them is greater than that of the other, namely these electrodes have different work functions. Accordingly, the work function of the electrode 2 may be relatively greater than that of the electrode 5. In this case, the difference in work function between the two electrodes is preferably 0.5 V or greater. In the case where a buffer layer is provided between each electrode and the adjacent semiconductor layer, and a compound of the buffer layer and the electrode are chemically bonded to each other, the above described restriction may sometimes be alleviated.

The electrodes 2 and 5 may be made of appropriately selected materials, including noble metals, e.g., gold, platinum, and silver; metal oxides, e.g., zinc oxide, indium oxide, tin oxide (NESA®), tin-doped indium oxide (ITO), and fluorine-doped tin oxide (FTO); lithium, lithium-indium alloys, sodium, sodium-potassium alloys, calcium, magnesium, magnesium-silver alloys, magnesium-indium alloys, indium, ruthenium, titanium, manganese, yttrium, aluminum, aluminum-lithium alloys, aluminum-calcium alloys, aluminum-magnesium alloys, chromium, graphite; and organic conductive compounds, such as poly(3,4-ethylenedioxythiophene)-poly(styrene sulfonate) (PEDOT:PSS). These electrode materials may be used either individually or as a mixture of two or more thereof. Since the electrode 2 must be transparent, transparent materials, such as zinc oxide, NESA, ITO, FTO, and PEDOT:PSS, are used. The electrodes 2 and 5 can be formed using these electrode materials by a dry or wet process similarly to the photoelectric layer 4. The electrodes 2 and 5 may also be formed through firing, for example, by the sol-gel process. The thickness of the electrodes 2 and 5, while varying depending on the material, usually ranges from about 5 to 1000 nm, preferably from about 10 to 500 nm.

The charge transfer layers 3 and 6 each serves to prevent the electrode material from entering and reacting with the photoelectric layer and to prevent charges separated in the photoelectric layer from recombining thereby to efficiently transfer the opposite charges to the electrodes 2 and 5. Materials used to form the charge transfer layers include PEDOT:PSS, PEO, $V_2O_5$, zinc oxide, lithium fluoride, $TiO_x$, naphthalene tetracarboxylic acid anhydride, and other charge transfer materials. The charge transfer layer 3 must be transparent. When the photoelectric layer 4 is of a P3HT:PCBM bulk heterojunction type, the charge transfer layer 3 is often formed of PEDOT:PSS, and the charge transfer layer 6 is often formed of LiF. The charge transfer layers 3 and 6 are formed by using these charge transfer materials by a dry or wet process similarly to the photoelectric layer 4. The thickness of each of the charge transfer layers 3 and 6 is usually 0.01 to 100 nm, preferably about 0.2 to 50 nm.

The photoelectric device of the invention finds use in not only organic thin film solar cells of the invention but also photodiodes, light detectors, and the like.

EXAMPLES

The invention will now be illustrated in greater detail with reference to Examples and Comparative Example, but it should be understood that the invention is not deemed to be limited thereto.

Example 1—Synthesis of Compound No. 11 ($R^1$ and $R^6$=$C_{12}H_{25}$; $R^2$, $R^3$, $R^4$, and $R^5$=H)

Step 1: Preparation of 2,9-bis(triisopropylsilyl) phenanthro[1,2-b:8,7-b']dithiophene (7a)

[Chem. 14]

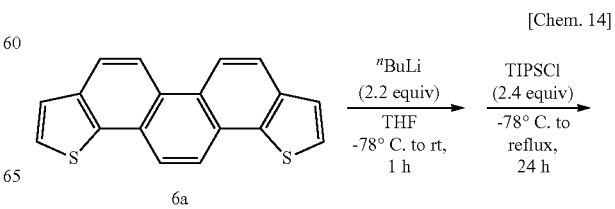

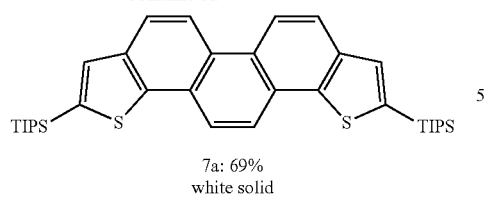

7a: 69%
white solid

A 50 ml shrenk tube was charged in an argon atmosphere with 809 mg (2.8 mmol, 1 equiv.) of phenanthro[1,2-b:8,7-b']dithiophene (PDT) (6a) and 50 ml of dehydrated THF, followed by cooling the contents to −78° C. Then, 3.85 ml of a 1.6M solution of n-BuLi (6.2 mmol, 2.2 equiv.) in hexane was added thereto dropwise. After the mixture was allowed to cool to room temperature, it was stirred for 1 hour, followed by cooling to −78° C. To the mixture was added dropwise 1.44 ml (6.7 mmol, 2.4 equiv.) of triisopropylsilyl chloride (TIPSCl), followed by refluxing for 24 hours. Water and 1N hydrochloric acid were added to the reaction system to quench the reaction. The reaction mixture was extracted with chloroform, and the organic layer was washed with a saturated sodium chloride aqueous solution and dried over anhydrous magnesium sulfate. The resulting mixed solution was filtered, and the solvent was removed on a rotary evaporator. The residue was purified by silica gel column chromatography to give the desired compound 7a as a white solid in a yield of 69% (1.17 g, 1.9 mmol). The conditions of silica gel column chromatography and analytical results of compound 7a were as follows.

Silica gel column chromatography: Rf=0.38; hexane m.p.: 98-100° C.

FT-IR (KBr, cm$^{-1}$): 2941 (w), 2989 (m), 2864 (w), 1564 (s), 1460 (m), 1284 (m), 1072 (m), 949 (w), 883 (m), 842 (m), 686 (m), 592 (m).

$^1$H-NMR (600 MHz, CDCl$_3$, rt): 1.20 (d, J=7.2 Hz, 36H), 1.55 (sept, J=7.2 Hz, 6H), 7.68 (2, 2H), 8.04 (d, J=8.4 Hz, 2H), 8.26 (s, 2H), 8.65 (d, J=9 Hz, 2H).

$^{13}$C[$^1$H]-NMR (150 MHz, CDCl$_3$, rt): 11.9, 18.7, 120.2, 122.2, 123.8, 126.8, 127.4, 133.5, 135.8, 138.9, 142.9.

$^{29}$Si[$^1$H]-NMR (119 MHz, CDCl$_3$, rt): 2.16.

Anal. Calcd. for $C_{36}H_{50}S_2Si_2$: C, 71.70; H, 8.36. Found: C, 71.72; H, 8.36.

Step 2: Preparation of 4,7-bis(4,4,5,5-tetramethyl-1,3,2-dioxaborolan-2-yl)-2,9-bis(triisopropylsilyl)phenanthro[1,2-b:8,7-b]dithiophene (8a)

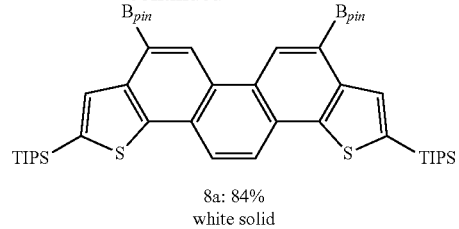

8a: 84%
white solid

A 50 ml shrenk tube was charged in an argon atmosphere with 50 mg (0.075 mmol, 5 mol %) of [Ir(OMe)(cod)]$_2$ ((1,5-cyclooctadiene)(methoxy)iridium (I) dimer), 40 mg (0.15 mmol, 10 mol %) of dtbpy (4,4-di-t-butyl bipyridine), 762 mg (3 mmol, 2 equiv.) of B$_2$pin$_2$ (bis(pinacolato)diboron), and 30 ml of dehydrated cyclohexane, followed by stirring at room temperature for 10 minutes. Then, 905 mg (1.5 mmol, 1 equiv.) of compound 7a was added thereto, followed by stirring in the dark at 80° C. for 10 hours. Water was added to the reaction system to quench the reaction. The reaction mixture was extracted with chloroform, and the organic layer was washed with a saturated sodium chloride aqueous solution and dried over anhydrous magnesium sulfate. The mixed solution was filtered, and the solvent was removed on a rotary evaporator. The residue was purified by silica gel column chromatography to give the desired compound 8a as a white solid in a yield of 84% (1.07 g, 1.26 mmol). The conditions of silica gel column chromatography and analytical results of compound 8a were as follows.

Silica gel column chromatography: Rf=0.54; hexane/ethyl acetate=5/1.

m.p.: 174-175° C.

FT-IR (KBr, cm$^{-1}$): 2943 (w), 2891 (m), 2866 (w), 1587 (m), 1463 (m), 1317 (w), 1303 (w), 1143 (w), 1099 (m), 974 (w), 846 (m), 680 (m), 605 (s).

$^1$H-NMR (600 MHz, CDCl$_3$, rt): 1.25 (d, J=7.8 Hz, 36H), 1.48-1.53 (m, 30H), 8.33 (s, 2H), 8.48 (s, 2H), 9.32 (s, 2H).

$^{13}$C[$^1$H]-NMR (150 MHz, CDCl$_3$, rt): 12.0, 18.7, 25.1, 83.9, 125.1, 126.9, 128.6, 129.2, 135.1, 136.1, 142.5, 142.7. The carbon signal adjacent to B was not observed due to low intensity.

$^{11}$B[$^1$H]-NMR (192 MHz, CDCl$_3$, rt): 31.6.

$^{29}$Si[$^1$H]-NMR (119 MHz, CDCl$_3$, rt): 1.96.

Anal. Calcd. for $C_{48}H_{72}B_2O_4S_2Si_2$: C, 67.43; H, 8.49. Found: C, 67.14; H, 8.52.

Step 3: Preparation of 4,7-dibromo-2,9-bis(triisopropylsilyl)phenanthro[1,2-b:8,7-b']dithiophene (9a)

[Chem. 15]

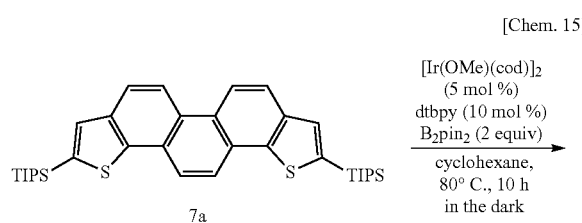

7a

[Ir(OMe)(cod)]$_2$ (5 mol %)
dtbpy (10 mol %)
B$_2$pin$_2$ (2 equiv)
cyclohexane,
80° C., 10 h
in the dark

[Chem. 16]

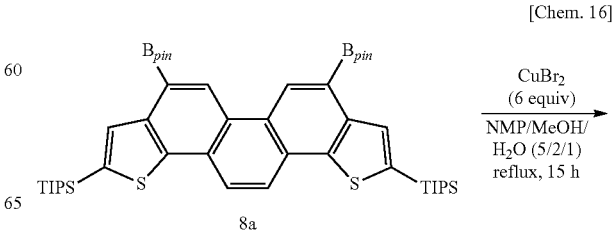

8a

CuBr$_2$ (6 equiv)
NMP/MeOH/H$_2$O (5/2/1)
reflux, 15 h

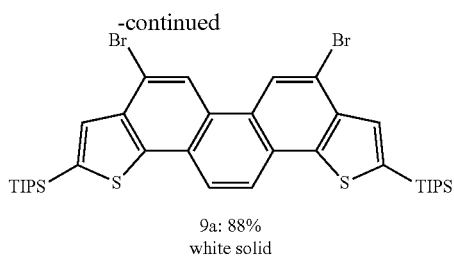

9a: 88%
white solid

A 50 ml Shrenk tube was charged with 1.07 g (1.25 mmol, 1 equiv.) of compound 8a, 1.68 g (7.5 mmol, 6 equiv.) of $CuBr_2$, and $NMP/MeOH/H_2O$ (15 ml/6 ml/3 ml), and the mixture was refluxed for 15 hours. The reaction was quenched by the addition of 1N hydrochloric acid. The precipitate was collected by filtration, washed with hexane, and dried to give 833 mg (1.1 mmol) of the desired compound 9a as a white solid in a yield of 88%. The analytical results of compound 9a are shown below.

m.p.: 184-185° C.

FT-IR (KBr, cm$^{-1}$): 2943 (w), 2889 (m), 2864 (w), 1548 (s), 1460 (m), 1087 (m), 954 (w), 881 (m), 648 (m), 599 (m)

$^1$H-NMR (600 MHz, CDCl$_3$, rt): 1.22 (d, J=7.2 Hz, 36H), 1.51 (sept, J=7.2 Hz, 6H), 7.79 (s, 2H), 8.09 (s, 2H), 8.66 (s, 2H).

$^{13}$C[$^1$H]-NMR (150 MHz, CDCl$_3$, rt): 11.9, 18.6, 116.8, 123.0, 123.6, 125.9, 127.3, 133.6, 137.3, 138.7, 143.3.

$^{29}$Si[$^1$H]-NMR (119 MHz, CDCl$_3$, rt): 2.55.

Anal. Calcd. for $C_{36}H_{48}Br_2S_2Si_2$: C, 56.83; H, 6.36. Found: C 56.83; H, 6.30

Step 4: Preparation of 4,7-didodecyl-2,9-bis(triisopropylsilyl)phenanthro[1,2-b:8,7-b']dithiophene (10a)

[Chem. 17]

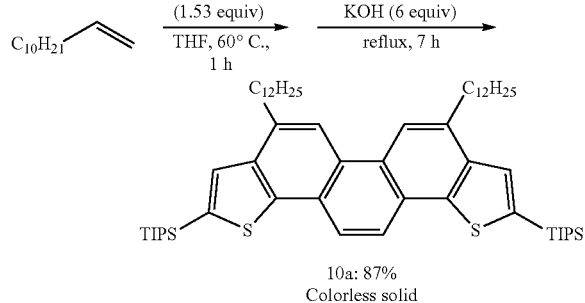

10a: 87%
Colorless solid

A 50 ml shrenk tube was charged in an argon atmosphere with 412 µl (1.86 mmol, 3 equiv.) of 1-dodecene, 232 mg (0.95 mmol, 1.53 equiv.) of 9-BBN dimer, and 12 ml of dehydrated THF, followed by stirring at 60° C. for 1 hour. After the reaction system was allowed to cool to room temperature, 472 mg (0.62 mmol, 1 equiv.) of compound 9a, 36 mg (0.03 mmol, 10 mol %) of Pd(dba)$_2$, 36 mg (0.06 mmol, 20 mol %) of [HPtBu$_3$]BF$_4$, and 209 mg (3.72 mmol, 6 equiv.) of potassium hydroxide were added thereto, followed by refluxing for 7 hours. The reaction was quenched by the addition of water, and the reaction mixture was extracted with chloroform. The organic layer was washed with a saturated sodium chloride aqueous solution and dried over anhydrous magnesium sulfate. The mixed solution was filtered, and the solvent was removed on a rotary evaporator. The residue was purified by silica gel column chromatography to give 506 mg (0.54 mmol) of the desired compound 10a as a colorless liquid in a yield of 87%. The conditions of silica gel column chromatography and analytical results of compound 10a were as follows.

Silica gel column chromatography: Rf=0.69; hexane.

FT-IR (KBr, cm$^{-1}$): 2924 (w), 2854 (w), 1573 (s), 1454 (w), 1382 (s), 999 (m), 883 (m), 650 (m), 500 (s).

$^1$H-NMR (600 MHz, CDCl$_3$, rt): 0.92 (t, J=7.2 Hz, 6H), 1.26 (d, J=7.8 Hz, 36H), 1.30-1.37 (m, 28H), 1.45 (quin, J=7.8 Hz, 4H), 1.51-1.57 (m, 10H), 1.93 (quin, J=7.8 Hz, 4H), 3.22 (t, J=7.8 Hz, 4H), 7.77 (s, 2H), 8.17 (s, 2H), 8.42 (s, 2H).

$^{13}$C[$^1$H]-NMR (150 MHz, CDCl$_3$, rt): 11.9, 14.1, 18.7, 22.7, 29.4, 29.6, 29.66, 29.69, 29.73, 29.75, 29.8, 31.1, 31.9, 35.0, 119.1, 122.8, 125.5, 127.5, 131.5, 134.8, 136.2, 138.6, 143.2.

$^{29}$Si[$^1$H]-NMR (119 MHz, CDCl$_3$, rt): 2.16.

Anal. Calcd. for $C_{60}H_{98}S_2Si_2$: C, 76.69; H, 10.51. Found: C, 76.72; H, 10.69.

Step 5: Preparation of 4,7-didodecylphenanthro[1,2-b:8,7-b']dithiophene (3a)

[Chem. 18]

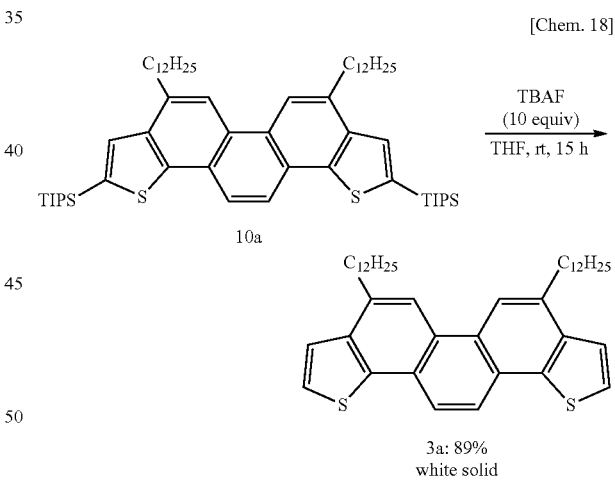

3a: 89%
white solid

A 50 ml Shrenk tube was charged in an argon atmosphere with 613 mg (0.65 mmol, 1 equiv.) of compound 10a, 6.5 ml (6.5 mmol, 10 equiv.) of TBAF (1M in THF), and 26 ml of dehydrated THF, followed by stirring at room temperature for 15 hours. The reaction was quenched by the addition of water, and the reaction mixture was extracted with chloroform. The organic layer was washed with a saturated sodium chloride aqueous solution and dried over anhydrous magnesium sulfate. The resulting mixed solution was filtered, and the solvent was removed on a rotary evaporator. The residue was purified by silica gel column chromatography to give 363 mg (0.58 mmol) of the desired compound 3a as a white solid in a yield of 89%. The conditions of silica gel column chromatography and analytical results of compound 3a were as follows.

Silica gel column chromatography: Rf=0.52; hexane.
m.p.: 84-86° C.
FT-IR (KBr, cm$^{-1}$): 3039 (m), 3072 (s), 3043 (s), 2954 (w), 2914 (w), 2848 (w), 1577 (s), 1469 (w), 1344 (s), 1153 (m), 854 (w), 802 (w), 694 (w).
$^1$H-NMR (600 MHz, CDCl$_3$, rt): 0.89 (t, J=7.8 Hz, 6H), 1.22-1.35 (m, 28H), 1.41 (quin, J=7.8 Hz, 4H), 1.51 (quin, J=7.8 Hz, 4H), 1.87 (quin, J=7.8 Hz, 4H), 3.17 (t, J=7.8 Hz, 4H), 7.56 (d, J=5.4 Hz, 2H), 7.60 (d, J=5.4 Hz, 2H), 8.11 (s, 2H), 8.43 (s, 2H).
$^{13}$C[$^1$H]-NMR (150 MHz, CDCl$_3$, rt): 14.1, 22.7, 29.4, 29.6, 29.65, 29.69, 29.71, 29.8, 31.1, 31.9, 35.0, 119.2, 122.6, 123.0, 125.1, 125.7, 127.7, 136.6, 137.3, 139.0.
Anal. Calcd. for C$_{42}$H$_{58}$S$_2$: C, 80.45; H, 9.32. Found: C, 80.51, H, 9.17.

Step 6: Preparation of 4,7-didodecyl-2,9-bis(trimethylstannyl)phenanthro[1,2-b:8,7-b']dithiophene (4a)

A 20 ml Shrenk tube was charged in an argon atmosphere with 188 mg (0.3 mmol, 1 equiv.) of compound 3a and 12 ml of dehydrated THF, followed by cooling to 0° C. To the mixture was then added dropwise 0.56 ml (0.9 mmol, 3 equiv.) of n-BuLi (1.6M in hexane), followed by refluxing for 2 hours. After stirring, the reaction mixture was cooled to 0° C., and 239 mg (1.2 mol, 4 equiv.) of Me$_3$SnCl was added thereto dropwise, followed by stirring at room temperature for 12 hours. The reaction was quenched by the addition of water, and the reaction mixture was extracted with dichloromethane. The organic layer was washed with a saturated sodium chloride aqueous solution and dried over anhydrous magnesium sulfate. The mixed solution was filtered, and the solvent was removed on a rotary evaporator. The residue was purified twice by high performance liquid chromatography to give 159 mg (0.17 mmol) of the desired compound 4a as a pale yellow liquid in a yield of 56%. The analytical results of compound 4a were as follows.

FT-IR (KBr, cm$^{-1}$): 2924 (w), 2852 (w), 1571 (s), 1465 (s), 1377 (s), 950 (s), 771 (m), 532 (m).
$^1$H-NMR (600 MHz, CDCl$_3$, rt): 0.46 (t, J=28.8 Hz, 18H), 0.88 (t, J=7.2 Hz, 6H), 1.22-1.36 (m, 28H), 1.43 (quin, J=7.8 Hz, 4H), 1.53 (quin, J=7.8 Hz, 4H), 1.90 (quin, J=7.8 Hz, 4H), 3.20 (t, J=7.8 Hz, 4H), 7.65 (s, 2H), 8.15 (s, 2H), 8.40 (s, 2H).
$^{13}$C[$^1$H]-NMR (150 MHz, CDCl$_3$, rt): 8.16 (t, JC-Sn=177 Hz), 14.1, 22.7, 29.4, 29.6, 29.67, 29.69, 29.72, 29.8, 31.0, 31.9, 35.0, 119.1, 122.8, 125.4, 127.2, 130.8, 136.0, 138.6, 138.8, 143.9.
Anal. Calcd. for C$_{48}$H$_{74}$S$_2$Sn$_2$: C, 60.52; H, 7.83. Found: C, 60.74; H, 7.96.

Step 7: Preparation of compound No. 11 (R$^1$ and R$^6$=C$_{12}$H$_{25}$; R$^2$, R$^3$, R$^4$, and R$^5$=H)

[Chem. 19]

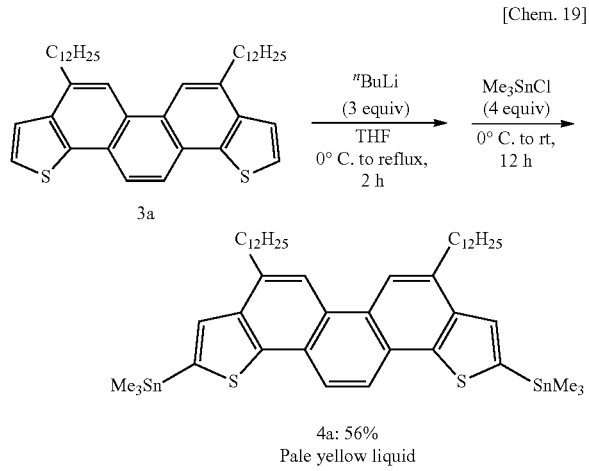

4a: 56%
Pale yellow liquid

[Chem. 20]

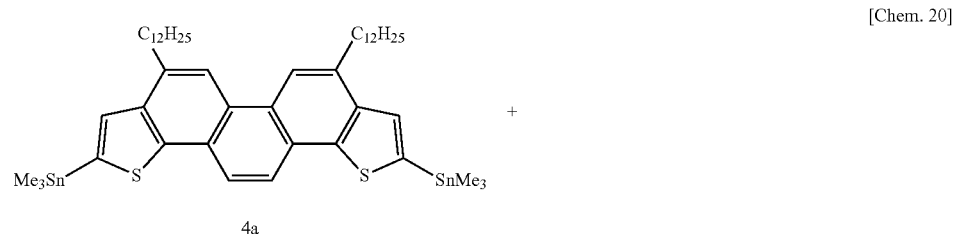

4a

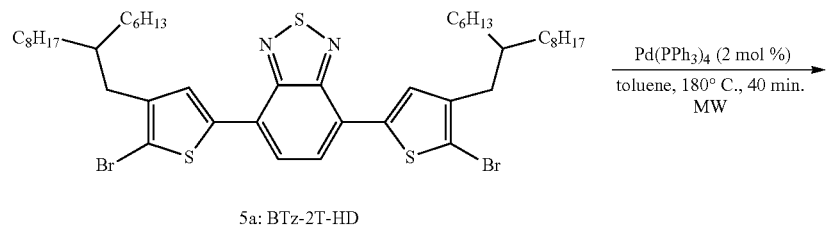

5a: BTz-2T-HD

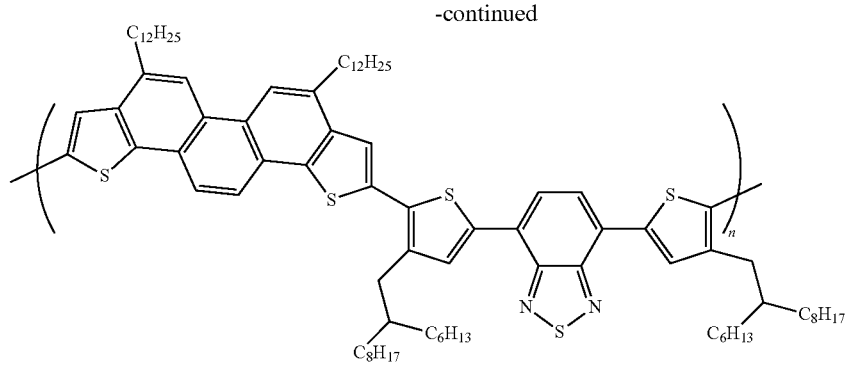

No. 11 77%
Blackish purple solid

A 5 ml vial tube was charged with 62.7 mg (0.066 mmol, 1 equiv.) of compound 4a, 59.7 mg (0.066 mmol, 1 equiv.) of BTz-2T-HD (compound 5a), and 1.5 mg (1.32 μmol, 2 mol %) of Pd(PPh$_3$)$_4$, filled with argon gas, and sealed with a stopper. To the tube was put 3.3 ml of dehydrated toluene, and the reaction system was stirred at 180° C. for 40 minutes under microwave irradiation in a microwave applicator. To the reaction mixture was added a mixture of 100 ml of methanol and 5 ml of hydrochloric acid, followed by stirring at room temperature for 3 hours. The precipitate was collected by filtration and Soxhlet-extracted successively with methanol, hexane, and chloroform each for 3 hours. The chloroform extract was evaporated on a rotary evaporator to remove the solvent and dried under reduced pressure to afford 69.7 mg (0.051 mmol) of the desired compound No. 11 as a blackish purple solid in a yield of 77%. The analysis results of compound No. 11 are shown below.

Anal. Calcd. for $C_{88}H_{128}N_2S_5$: C, 76.91; H, 9.39; N, 2.04. Found: C, 76,54; H, 9.26; N, 1.99.

Mw/Mn=31443/21602 (measuring conditions: 140° C., o-DCB)

Example 2—Synthesis of Compound No. 16 ($R^1$ and $R^6$=$C_{12}H_{25}$; $R^2$, $R^3$, $R^4$, and $R^5$=H)

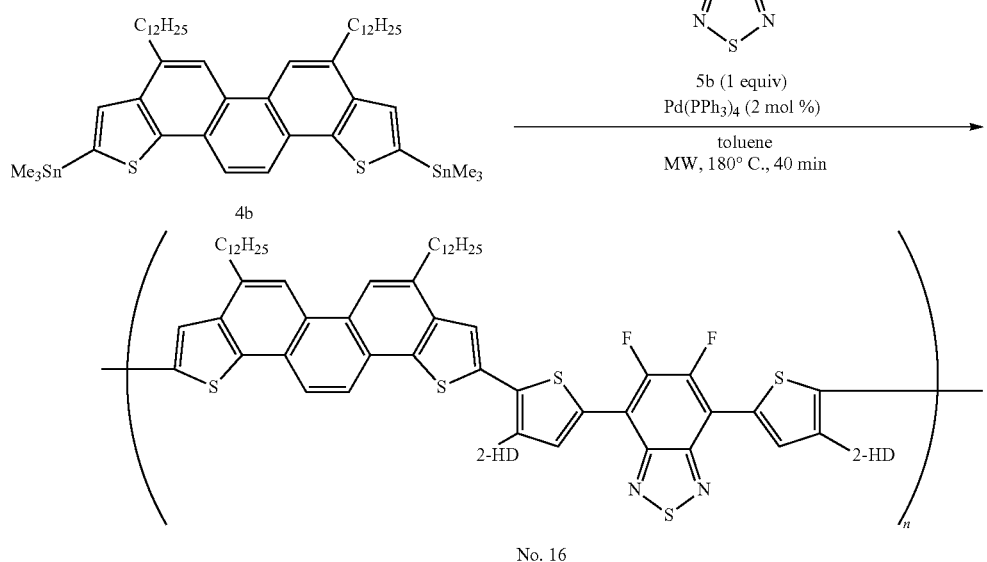

Compound 4b was synthesized by the same processes of steps 1 through 6 of Example 1. A 5 ml reaction vessel was charged with 56.1 mg (0.059 mmol) of compound 4b, 55.5 mg (0.059 mmol) of compound 5b, and 1.4 mg (1.2 μmol) of Pd(PPh$_3$)$_4$, filled with argon gas, and sealed. To the vessel was added 2.5 ml of toluene, and the mixture was stirred at 180° C. for 40 minutes in a microwave reactor. After the reaction mixture was cooled to room temperature, it was poured into a mixture of 100 ml of methanol and 5 ml of concentrated hydrochloric acid, followed by stirring at room temperature for 3 hours. The precipitate thus formed was collected by filtration and Soxhlet-extracted successively with methanol, hexane, chloroform, and chlorobenzene. The chloroform extract and the chlorobenzene extract were each concentrated, and reprecipitated in methanol. The precipitate was collected by filtration and dried under reduced pressure to give 37.9 mg (yield: 46%) of the desired chloroform-soluble compound No. 16 as a purple solid with a metallic luster. The analytical results of compound No. 16 were as follows.

GPC (o-DCB, 140° C.): $M_n$=30.6 kDa, PDI=2.05 (CHCl$_3$); $M_n$=42.3 kDa, PDI=1.82 (PhCl)

Example 3—Synthesis of Compound No. 17 ($R^1$ and $R^6$=$C_{12}H_{25}$; $R^2$, $R^3$, $R^4$, and $R^5$=H)

reduced pressure to give 90.7 mg (yield: 89%) of the desired chloroform-soluble compound No. 17 as a purple solid with a metallic luster. The analytical results of compound No. 17 were as follows.

GPC (o-DCB, 140° C.): $M_n$=22.8 kDa, PDI=1.39.

Examples 4 and 5 and Comparative Example 1

Fabrication and Evaluation of Organic Thin Film Solar Cell Device

An ITO substrate (thickness: 150 nm; resistivity: <12 Ω/sq; transmittance (λ=550 nm): ≥85%; available from Geomatec Co., Ltd.) was ultrasonically cleaned successively in ion-exchanged water, acetone, and isopropyl alcohol each for 10 minutes. The isopropyl alcohol in which the substrate was placed was then boiled for 10 minutes. The substrate was dried and cleaned by UV/ozone for 20 minutes. On the thus cleaned substrate was dropped an aqueous solution of PEDOT:PSS (Clevios PVPAI 4083) through a 0.45 μm

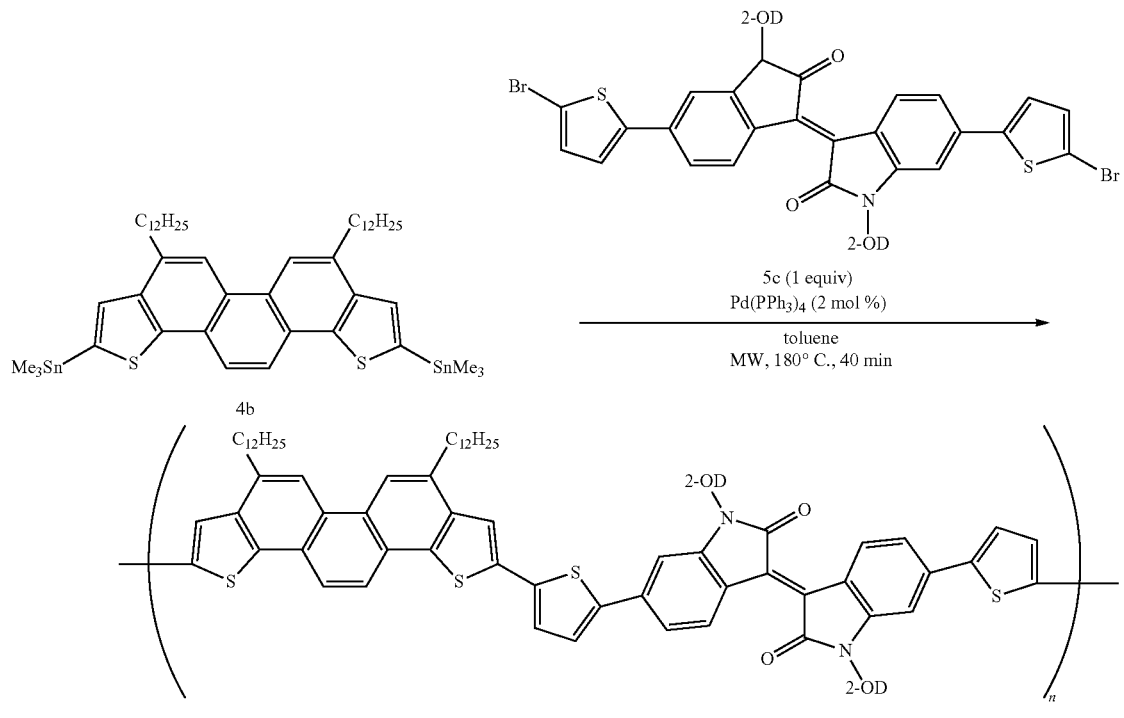

Compound 4b was synthesized by the same processes of steps 1 through 6 of Example 1. A 5 ml reaction vessel was charged with 60.0 mg (0.063 mmol) of compound 4b, 72.1 mg (0.063 mmol) of compound 5c, and 1.5 mg (1.2 μmol) of Pd(PPh$_3$)$_4$, filled with argon gas, and sealed. To the vessel was added 2.9 ml of toluene, and the mixture was stirred at 180° C. for 40 minutes in a microwave reactor. After the reaction mixture was cooled to room temperature, it was poured into a mixture of 100 ml of methanol and 5 ml of concentrated hydrochloric acid, followed by stirring at room temperature for 3 hours. The precipitate thus formed was collected by filtration and Soxhlet-extracted successively with methanol, hexane, and chloroform. The chloroform extract was concentrated, and reprecipitated in methanol. The precipitate was collected by filtration and dried under syringe filter made of PVDF, spun at 5000 rpm for 30 seconds, and baked on a hot plate at 120° C. for 10 minutes to form a positive electrode buffer layer. Immediately after the baking, the coated substrate was placed in a glove box. A soluble fullerene derivative (PC$_{61}$BM) as component (B) was added to a 10 g/l solution of compound No. 16 (component (A)) synthesized in Example 2 in anhydrous chlorobenzene in an (A) to (B) weight ratio of 1:1 or 1:2. The resulting mixed solution, while being maintained at 100° C., was applied to the PEDOT:PSS-coated substrate by spin coating at 400 rpm for 30 minutes and then at 1000 rpm for 5 seconds to form an active layer. After drying at room temperature, the coated substrate was transferred to a vacuum deposition chamber. Calcium and aluminum were successively vacuum deposited on the active layer under reduced pressure (about 3×10⁻⁵ Pa) through a shadow mask to a thickness of 10 nm and 80 nm, respectively, as a negative electrode buffer layer and a negative electrode, respectively, to make a bulk heterojunction solar cell device with an active area of 0.16 cm⁻². The photoelectric conversion efficiency of the resulting bulk heterojunction solar cell device was determined by irradiating the ITO electrode side of the device with pseudo-sunlight (AM 1.5 G, 100 mW/cm²).

For comparison, a solar cell device was fabricated and evaluated for photoelectric efficiency in the same manner as in Examples 4 and 5, except for replacing compound No. 16 with compound A shown below. The results obtained are shown in Table 1.

TABLE 1

| | Component (A) | Component (B) | Conversion Efficiency (%) | (A)/(B) |
|---|---|---|---|---|
| Example 4 | No. 16 | PCBM | 5.07 | 1/1 |
| Example 5 | No. 16 | PCBM | 4.23 | 1/2 |
| Comparative Example 1 | compound A | PCBM | 2.01 | 1/1 |

Compound A:

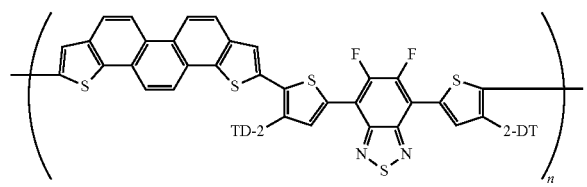

It was thus verified that, when the picene derivative of the invention obtained in Examples is used as a p-type organic semiconductor, a high photoelectric efficiency is obtained

DESCRIPTION OF REFERENCE NUMERALS

1 Substrate
2 Electrode
3 Charge transfer layer
4 Photoelectric layer
5 Electrode
6 Charge transport layer

The invention claimed is:

1. A picene derivative comprising 2 to 100 constitutional units represented by general formula (1):

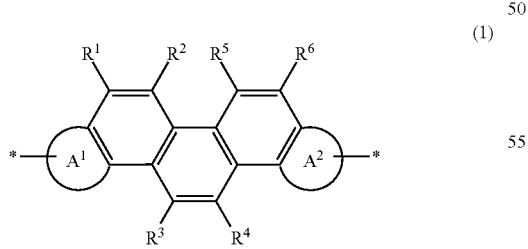

wherein $A^1$ and $A^2$ each independently represent a monocyclic ring; $R^1$, $R^2$, $R^3$, $R^4$, $R^5$, and $R^6$ each independently represent a hydrogen atom, a halogen atom, a cyano group, a nitro group, a hydroxy group, a carboxyl group, a thiol group, —$SiR^7R^8R^9$, —$NR^{10}R^{11}$, or an optionally substituted hydrocarbon group, provided that at least one of $R^1$, $R^2$, $R^3$, $R^4$, $R^5$, and $R^6$ is not hydrogen; and $R^7$, $R^8$, $R^9$, $R^{10}$, and $R^{11}$ each independently represent a hydrogen atom or an optionally substituted hydrocarbon group.

2. The picene derivative according to claim 1, wherein said picene derivative comprises 2 to 100 constitutional units represented by the above formula (1) and at least one constitutional unit selected from the constitutional units of group Y and group Z:

<Group Y>

(Y-1)

(Y-2)

(Y-3)

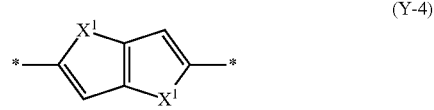
(Y-4)

(Y-5)

(Y-6)

(Y-7)

(Y-8)

wherein $X^1$ and $X^4$ each represent S, O, or $NR^{12}$; k represents an integer of 1 to 4; $R^{12}$ represents an optionally substituted hydrocarbon group; the hydrogen atom of the constitutional unit of group Y is optionally replaced with a halogen atom, a cyano group, a nitro group, a hydroxy group, a carboxyl group, a thiol group, —$NR^{13}R^{14}$, an optionally substituted hydrocarbon group, or an optionally substituted heterocyclic group; and $R^{13}$ and $R^{14}$ each represent an optionally substituted hydrocarbon group; and <Group Z>
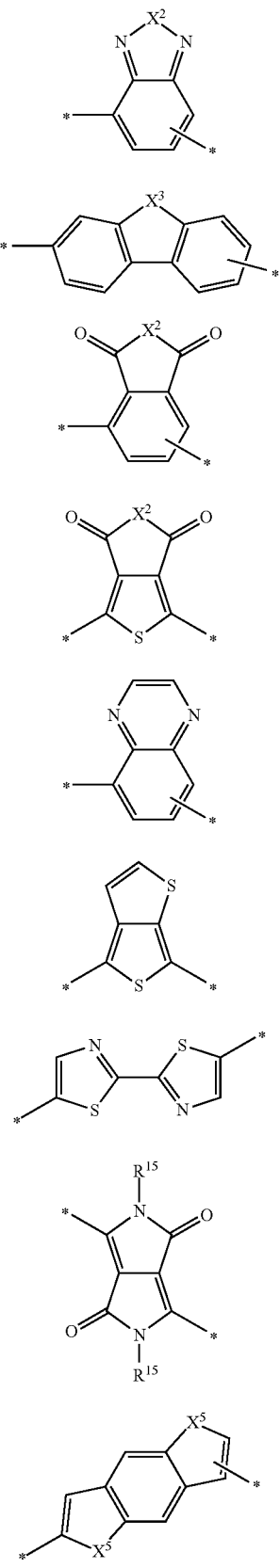
(Z-1)
(Z-2)
(Z-3)
(Z-4)
(Z-5)
(Z-6)
(Z-7)
(Z-8)
(Z-9)
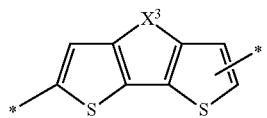
(Z-10)
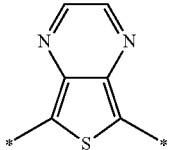
(Z-11)
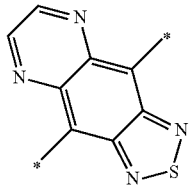
(Z-12)
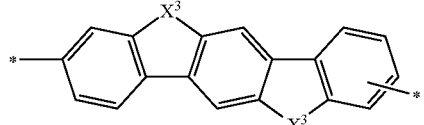
(Z-13)
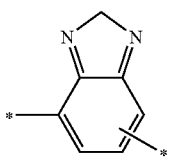
(Z-14)
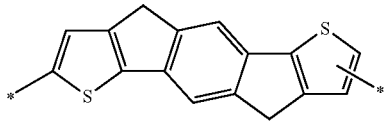
(Z-15)
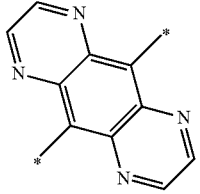
(Z-16)
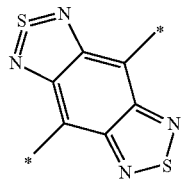
(Z-17)
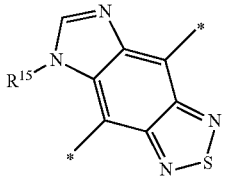
(Z-18)

-continued

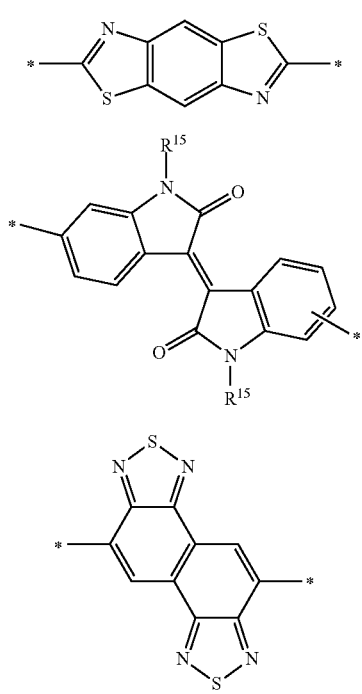

(Z-19)

(Z-20)

(Z-21)

wherein $X^2$ represents S or $NR^{15}$; $X^3$ represents S, $NR^{15}$, $CR^{16}R^{17}$, or $SiR^{16}R^{17}$; $X^5$ represents S, O, or $NR^{15}$; $R^{15}$, $R^{16}$, and $R^{17}$ each represent an optionally substituted hydrocarbon group; the hydrogen atom of the constitutional unit of group Z is optionally replaced with a halogen atom, a cyano group, a nitro group, a hydroxy group, a carboxyl group, a thiol group, —$NR^{18}R^{19}$, an optionally substituted hydrocarbon group, or an optionally substituted heterocyclic group; and $R^{16}$ and $R^{19}$ each represent an optionally substituted hydrocarbon group.

3. A photoelectric material comprising (A) the picene derivative according to claim 2 as a p-type organic semiconductor material and (B) an n-type organic semiconductor material.

4. The picene derivative according to claim 1, comprising 2 to 100 constitutional unit represented by general formula (2):

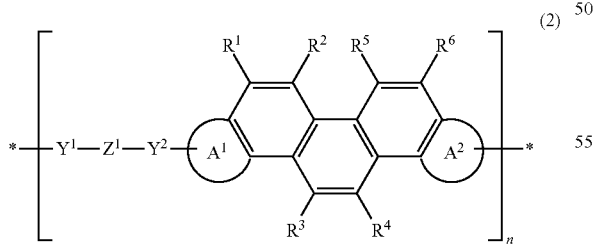

(2)

wherein $A^1$, $A^2$, $R^1$, $R^2$, $R^3$, $R^4$, $R^5$, and $R^6$ are as defined in claim 1; at least one $R^1$, $R^2$, $R^3$, $R^4$, $R^5$, and $R^6$ is not hydrogen; $Y^1$ and $Y^2$ each represent a single bond or a combination of 1 to 5 groups selected from (Y-1) to (Y-8) linked to each other; $Z^1$ represents a single bond or a group selected form (Z-1) to (Z-21); and n represents an integer of 1 to 1000:

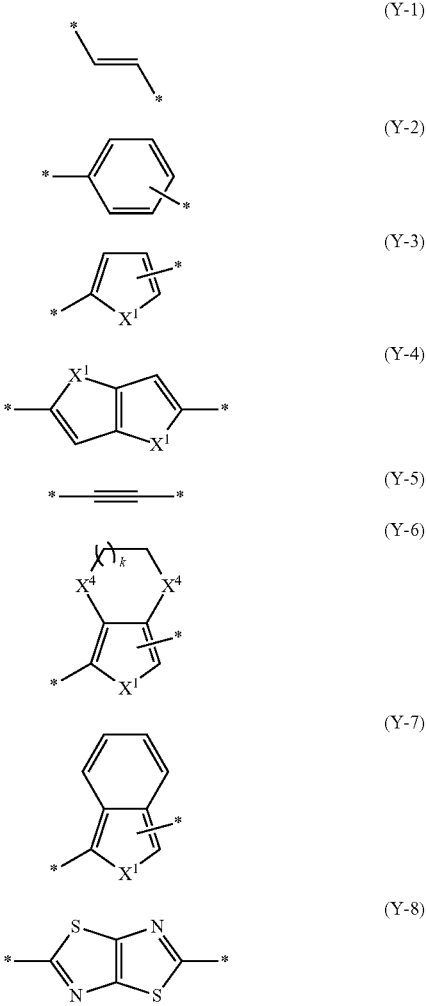

(Y-1)

(Y-2)

(Y-3)

(Y-4)

(Y-5)

(Y-6)

(Y-7)

(Y-8)

wherein $X^1$ and $X^4$ each represent S, O, or $NR^{12}$; k represents an integer 1 to 4; $R^{12}$ represents an optionally substituted hydrocarbon group; the hydrogen atom of the groups (Y-1) to (Y-4) and (Y-6) to (Y-8) is optionally replaced with a halogen atom, a cyano group, a nitro group, a hydroxy group, a carboxyl group, a thiol group, —$NR^{13}R^{14}$, an optionally substituted hydrocarbon group, or an optionally substituted heterocyclic group; and $R^{13}$ and $R^{14}$ each represent an optionally substituted hydrocarbon group:

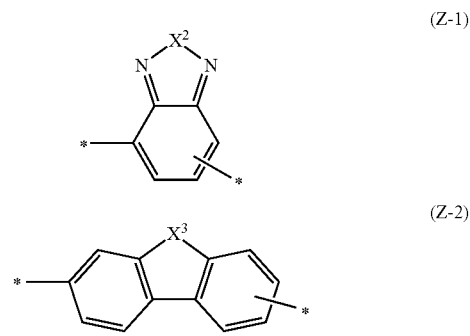

(Z-1)

(Z-2)

-continued
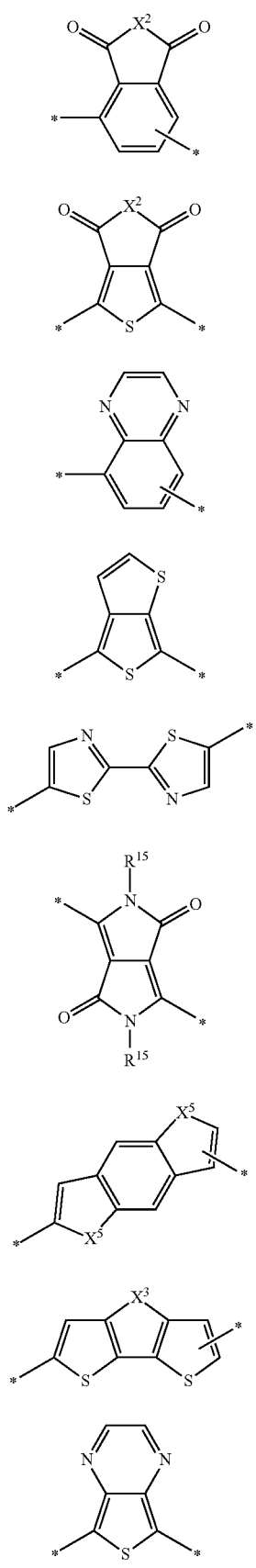
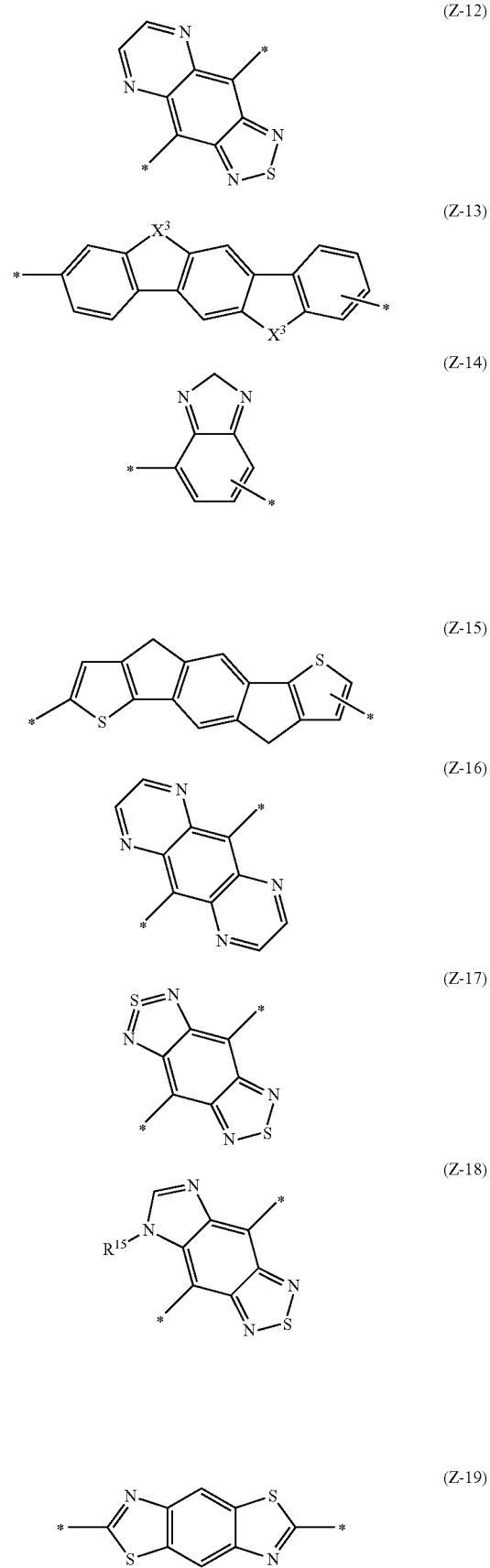

-continued

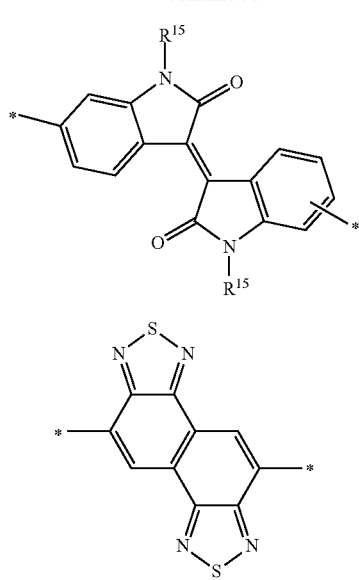

(Z-20)

(Z-21)

wherein $X^2$ represents S or $NR^{15}$, $X^3$ represents S, $NR^{15}$, $CR^{16}R^{17}$, or $SiR^{16}R^{17}$; $X^5$ represents S, O, or $NR^{15}$;

$R^{15}$, $R^{16}$, and $R^{17}$ each represent an optionally substituted hydrocarbon group; the hydrogen atom of the groups (Z-1) to (Z-21) is optionally replaced with a halogen atom, a cyano group, a nitro group, a hydroxy group, a carboxyl group, a thiol group, —$NR^{18}R^{19}$, an optionally substituted hydrocarbon group, or an optionally substituted heterocyclic group; and $R^{18}$ and $R^{19}$ each represent an optionally substituted hydrocarbon group.

5. A photoelectric material comprising (A) the picene derivative according to claim 4 as a p-type organic semiconductor material and (B) an n-type organic semiconductor material.

6. A photoelectric material comprising (A) the picene derivative according to claim 1 as a p-type organic semiconductor material and (B) an n-type organic semiconductor material.

7. A photoelectric layer obtained by film formation using the photoelectric material according to claim 6.

8. A photoelectric device comprising the photoelectric layer according to claim 7.

9. An organic thin film solar cell comprising the photoelectric device according to claim 8.

* * * * *